United States Patent [19]

Missbach

[11] Patent Number: 5,869,485
[45] Date of Patent: Feb. 9, 1999

[54] PYRROLO[2,3-D]PYRIMIDINES AND THEIR USE

[75] Inventor: Martin Missbach, Rheinfelden, Switzerland

[73] Assignee: Novartis Finance Corp., New York, N.Y.

[21] Appl. No.: 793,313

[22] PCT Filed: Sep. 8, 1995

[86] PCT No.: PCT/EP95/03536

§ 371 Date: Mar. 19, 1997

§ 102(e) Date: Mar. 19, 1997

[87] PCT Pub. No.: WO96/10028

PCT Pub. Date: Apr. 4, 1996

[30] Foreign Application Priority Data

Sep. 29, 1994 [CH] Switzerland .............................. 2953/94

[51] Int. Cl.⁶ ...................... A61K 31/505; C07D 487/04; C07D 207/34
[52] U.S. Cl. ...................... 514/234.2; 514/258; 544/117; 544/280; 548/558
[58] Field of Search .................................. 544/117, 280; 514/234.2, 258

[56] References Cited

FOREIGN PATENT DOCUMENTS

| 0635507A1 | 1/1995 | European Pat. Off. . |
| 0682027A1 | 11/1995 | European Pat. Off. . |
| 9519774 | 7/1995 | WIPO . |

OTHER PUBLICATIONS

Dave, et al., Indian Journal of Chemistry, vol. 27B, Aug. 1988, pp. 778–780.

Dave, et al., J. Indian Chem. Soc., vol. LXIV, Nov. 1987, pp. 713–715.

Roth, et al, Arch. Pharm., vol. 308, 1975, pp. 252–258.

Marquet, et al., Chim. Therapeutique, 1971, vol. 6, pp. 427–438.

*Primary Examiner*—Mark L. Berch
*Attorney, Agent, or Firm*—Gregory D. Ferraro

[57] ABSTRACT

The invention relates to the use of the compounds mentioned below in the therapeutic treatment of tumor diseases and other proliferative diseases, such as psoriasis, and to novel compounds of that type. The compounds are compounds of formula I

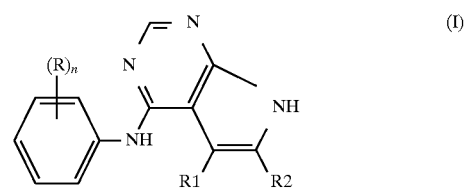

wherein n is from 0 to 5 and, when n is not 0, R is one or more substituents selected from halogen, alkyl, trifluoromethyl and alkoxy; and $R_1$ and $R_2$ are each independently of the other alkyl, or phenyl that is unsubstituted or substituted by halogen, trifluoromethyl, alkyl or by alkoxy, it also being possible for one of the two radicals $R_1$ and $R_2$ to be hydrogen, or R1 and R2 together form an alkylene chain having from 2 to 5 carbon atoms that is unsubstituted or substituted by alkyl; or salts thereof. Compounds of formula I inhibit protein kinases, for example the tyrosine protein kinase of the receptor for the epidermal growth factor, EGF.

9 Claims, No Drawings

PYRROLO[2,3-D]PYRIMIDINES AND THEIR USE

This is a 371 of PCT/EP95/03536, filed Sep. 8, 1995. The invention relates to compounds of the formula I,

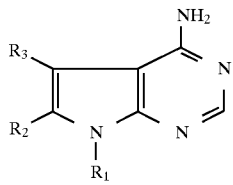

in which
R$_1$ is aryl;
R$_2$ is hydrogen, lower allyl or halogen; and
R$_3$ is aryl;
with the proviso that R$_3$ is other than phenyl, 4-methoxyphenyl and 4-chlorophenyl if R$_2$ is hydrogen and R$_1$ is phenyl, 4-methylphenyl, 4-methoxyphenyl, 4-chlorophenyl, 4-bromophenyl or 4-iodophenyl;
and salts thereof, processes for the preparation of these compounds, pharmaceutical compositions which contain these compounds, and the use of these compounds for the therapeutic treatment of the human or animal body or for the preparation of pharmaceutical compositions.

In the context of the present application, the general terms used above and below preferably have the following meanings:

the prefix "lower" designates a radical having up to and including 7, and in particular up to and including 4, carbon atoms.

Lower alkyl is, for example, n-propyl, isopropyl, n-butyl, isobutyl, sec-butyl, tert-butyl, n-pentyl, neopentyl, n-hexyl or n-heptyl, preferably ethyl or methyl.

Halogen is, for example, chlorine, bromine or fluorine, but can also be iodine.

Halo-lower alkyl is, for example, halomethyl, for example chloromethyl, or, for example, trifluoromethyl.

Lower alkanoyl is, for example, acetyl, propionyl or pivaloyl, but can also be, for example, formyl.

Aryl is, for example, phenyl or naphthyl, each of which is unsubstituted or substituted, e.g. as indicated below for phenyl. Aryl is preferably phenyl which is unsubstituted or substituted by one or more, e.g., 1–3, in particular one or two, substituents from the group consisting of lower alkyl, halo-lower alkyl, (hydroxy or lower alkanoyloxy)-lower alkyl, lower alkoxy-lower alkyl, (hydroxy, lower alkoxy or lower alkanoyloxy)-lower alkoxy-lower alkyl, (amino, lower alkylamino, di-lower alkylamino or lower alkanoylamino)-lower alkoxy-lower alkyl, (amino or lower alkanoylamino)-lower alkyl, lower alkylamino-lower alkyl, di-lower alkylamino-lower alkyl; azacycloalkyl-lower alkyl, e.g. (piperidinyl, piperazinyl, morpholinyl or pyrrolidinyl)-lower alkyl; azaheteroaryl-lower alkyl, e.g. (imidazolyl, triazolyl, pyridyl, pyrimidinyl or pyrrolyl)-lower alkyl, (hydroxy, lower alkoxy or lower alkanoyloxy)-lower alkylamino-lower alkyl, (amino, lower alkylamino, di-lower alkylamino or lower alkanoylamino)-lower alkylamino-lower alkyl; azacycloalkyl-lower alkylamino-lower alkyl, e.g. (piperidinyl, piperazinyl, morpholinyl or pyrrolidinyl)-lower alkylamino-lower alkyl; azaheteroaryl-lower alkylamino-lower alkyl, e.g. (imidazolyl, triazolyl, pyridyl, pyrimidinyl or pyrrolyl)-lower alkylamino-lower alkyl; mercapto-lower alkyl, lower alkyl-(thio, sulfinyl or sulfonyl) -lower alkyl, (hydroxy, lower alkoxy or lower alkanoyloxy) -lower alkyl-(thio, sulfinyl or sulfonyl)-lower alkyl, (amino, lower alkylamino, di-lower alkylamino or lower alkanoylamino)-lower alkyl-(thio, sulfinyl or sulfonyl)-lower alkyl, carboxy-lower alkyl, lower alkoxycarbonyl-lower alkyl, aminocarbonyl-lower alkyl, N-lower alkylaminocarbonyl-lower alkyl, N,N-di-lower alkylaminocarbonyl-lower alkyl, hydroxyl, lower alkoxy, lower alkanoyloxy, C$_1$–C$_3$alkylenedioxy, phenyl-lower alkoxy, (hydroxy, lower alkoxy or lower alkanoyloxy)-lower alkoxy, (amino or lower alkanoylamino)-lower alkoxy, lower alkylamino-lower alkoxy, di-lower alkylamino-lower alkoxy; azacycloalkyl-lower alkoxy, e.g. (piperidinyl, piperazinyl, morpholinyl or pyrrolidinyl)-lower alkoxy; azaheteroaryl-lower alkoxy, e.g. (imidazolyl, triazolyl, pyridyl, pyrimidinyl or pyrrolyl)-lower alkoxy; (hydroxy, lower alkoxy or lower alkanoyloxy)-lower alkylamino-lower alkoxy, (amino, lower alkylamino, di-lower alkylamino or lower alkanoylamino)-lower alkylamino-lower alkoxy; azacycloalkyl-lower alkylamino-lower alkoxy, e.g. (piperidinyl, piperazinyl, morpholinyl or pyrrolidinyl)-lower alkylamino-lower alkoxy; azaheteroaryl-lower alkylamino-lower alkoxy, e.g. (imidazolyl, triazolyl, pyridyl, pyrimidinyl or pyrrolyl)-lower alkylamino-lower alkoxy; (hydroxy, lower alkoxy or lower alkanoyloxy)-lower alkoxy-lower alkoxy, (amino, lower alkylamino, di-lower alkylamino or lower alkanoylamino)-lower alkoxy-lower alkoxy, (hydroxy, lower alkoxy or lower alkanoyloxy) -lower alkyl-(thio, sulfinyl or sulfonyl)-lower alkoxy, (amino, lower alkylamino, di-lower alkylamino or lower alkanoylamino)-lower alkyl-(thio, sulfinyl or sulfonyl)-lower alkoxy, hydroxysulfonyl-lower alkoxy, carboxy-lower alkoxy, lower alkoxycarbonyl-lower alkoxy, aminocarbonyl-lower alkoxy, N-lower alkylaminocarbonyl-lower alkoxy, N,N-di-lower alkylaminocarbonyl-lower alkoxy, amino, lower alkylamino, di-lower alkylamino, lower alkanoylamino; azacycloalkyl, e.g. piperidinyl, piperazinyl, morpholinyl or pyrrolidinyl; azaheteroaryl, e.g. imidazolyl, triazolyl, pyridyl, pyrimidinyl or pyrrolyl; mercapto, lower alkyl-(thio, sulfinyl or sulfonyl), (hydroxy, lower alkoxy or lower alkanoyloxy)-lower alkyl-(thio, sulfinyl or sulfonyl), (amino, lower alkylamino, di-lower alkylamino or lower alkanoylamino)-lower alkyl-(thio, sulfinyl or sulfonyl), (hydroxy, lower alkoxy or lower alkanoyloxy) -lower alkoxy-lower alkyl-(thio, sulfinyl or sulfonyl), (amino, lower alkylamino, di-lower alkylamino or lower alkanoylamino)-lower alkoxy-lower alkyl-(thio, sulfinyl or sulfonyl), (hydroxy, lower alkoxy or lower alkanoyloxy)-lower alkylamino-lower alkyl-(thio, sulfinyl or sulfonyl), (amino, lower alkylamino, di-lower alkylamino or lower alkanoylamino)-lower alkylamino-lower alkyl-(thio, sulfinyl or sulfonyl), carboxy-lower alkylthio, lower alkoxycarbonyl-lower alkylthio, aminocarbonyl-lower alkylthio, N-lower alkylaminocarbonyl-lower alkylthio, N,N-di-lower alkylaminocarbonyl-lower alkylthio, halogen, carboxyl, lower alkoxycarbonyl, aminocarbonyl, N-lower alkylaminocarbonyl, N-[(hydroxy, lower alkoxy or lower alkanoyloxy)-lower alkyl]-aminocarbonyl, N-[(amino, lower alkylamino, di-lower alkylamino or lower alkanoylamino)-lower alkyl]-aminocarbonyl; [azacycloalkyl-lower alkyl]-aminocarbonyl, e.g. N-[(piperidinyl, piperazinyl, morpholinyl or pyrrolidinyl)-lower alkyl]-aminocarbonyl; [azaheteroaryl-lower alkyl]-aminocarbonyl, e.g. N-[(imidazolyl, triazolyl, pyridyl, pyrimidinyl or pyrrolyl)-lower alkyl]-aminocarbonyl; N-(hydroxysulfonyl-lower alkyl)-aminocarbonyl, N,N-di-lower alkylaminocarbonyl, cyano, amidino, formamidino and guanidino and also, for example, nitro, lower alkanoyl and benzoyl.

Hydroxysulfonyl is the group —SO$_3$H. Aminocarbonyl is —CONH$_2$. Amidino is —C(=NH)—NH$_2$, formamidino is —NH—CH(=NH) and guanidino is —NH—C(=NH)—NH$_2$.

In substituents which contain groups such as hydroxy-lower alkoxy, amino-lower alkoxy, hydroxy-lower alkylamino, amino-lower alkylamino, hydroxy-lower alkylthio or amino-lower alkylthio, the two heteroatoms are preferably each separated by at least two C atoms, in other words: the lower alkyl moiety is in each case preferably selected such that there are at least two C atoms between the two heteroatoms.

Azacycloalkyl is a cycloalkyl radical having 3–8, in particular 5–7, ring atoms, in which at least one of the ring atoms is a nitrogen atom. Azacycloalkyl can additionally contain further ring heteroatoms, e.g. N, O or S; it is, for example, piperidinyl, piperazinyl, morpholinyl or pyrrolidinyl.

Azaheteroaryl is an aromatic radical having 3–7, in particular 5–7, ring atoms, in which at least one of the ring atoms is a nitrogen atom. Azaheteroaryl can additionally contain further ring heteroatoms, e.g. N, O or S. It can also be partially saturated. Azaheteroaryl is, for example, imidazolyl, triazolyl, pyridyl, pyrimidinyl or pyrrolyl.

Radicals such as piperidinyl, piperazinyl, morpholinyl, pyrrolidinyl, imidazolyl, triazolyl and pyrrolyl can be bonded via a ring nitrogen atom or a ring carbon atom; radicals such as pyridyl or pyrimidinyl are preferably bonded via a C atom.

As is known, the azacycloalkyl radicals bonded via a ring nitrogen atom, which are preferred, are designated as piperidino, piperazino, morpholino, pyrrolidino, etc.

Salts of compounds of the formula I are in particular pharmaceutically acceptable salts, primarily acid addition salts with suitable mineral acids, such as hydrohalic acids, sulfuric acid or phosphoric acid, e.g. hydrochlorides, hydrobromides, sulfates, hydrogen sulfates or phosphates, salts with suitable aliphatic or aromatic sulfonic acids or N-substituted sulfamic acids, e.g. methanesulfonates, benzenesulfonates, p-toluenesulfonates or N-cyclohexylsulfamates (cyclamates), or salts with strong organic carboxylic acids, such as lower alkanecarboxylic acids or aliphatic dicarboxylic acids which may be unsaturated or hydroxylated, e.g. acetates, oxalates, malonates, maleates, fumarates, tartrates or citrates.

If the compounds of the formula I contain an acidic group, corresponding salts with bases are also possible, e.g. corresponding alkali metal or alkaline earth metal salts, e.g. sodium, potassium or magnesium salts, pharmaceutically acceptable transition metal salts, such as zinc or copper salts, or salts with ammonia or organic amines, such as cyclic amines, such as mono-, di- or tri-lower alkylamines, such as hydroxy-lower alkylamines, e.g. mono-, di- or trihydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable mono-lower alkylamines are, for example, ethylamine and t-butylamine, suitable di-lower alkylamines, for example, diethylamine and diisopropylamine and suitable tri-lower alkylamines are, for example, trimethylamine and triethylamine. Corresponding hydroxy-lower alkylamines are, for example, mono-, di- and triethanolamine; hydroxy-lower alkyl-lower alkylamines are, for example, N,N-dimethylamino- and N,N-diethylaminoethanol. Compounds of the formula I having an acidic group, e.g. carboxyl, and a basic group, e.g. amino, can also exist, for example, in the form of internal salts, i.e. in zwitterionic form, or a part of the molecule can exist as an internal salt, and another part as a normal salt. Salts which are unsuitable for pharmaceutical uses are also included, as these can be used, for example, for the isolation or purification of free compounds I and of their pharmaceutically acceptable salts.

The compounds of the formula I have useful pharmacological properties. In particular, they inhibit the activity of the protein tyrosine kinase $pp60^{c-src}$ in concentrations between about 0.001 and about 10 $\mu$M [test description: K. Farley et al., Anal. Biochem. 203 (1992) 151–157; purified enzyme—as described in N. B. Lydon et al., Biochem. J. 287 (1992) 985–993—is used here].

It is known that both a specific change in the c-src gene, with leads to the elimination of c-src, and inhibition of the activity of the protein tyrosine kinase $pp60^{c-src}$ affects the bone resorption capability of osteoclasts [elimination of c-src by genetic manipulation: see, for example, P. Soriano et al., Cell 64 (1991) 693–702; inhibition of the activity of the protein tyrosine kinase $pp60^{c-src}$: see, for example, B. F. Boyce et al., J. Clin. Invest. 90 (1992) 1622–1627; T. Yoneda et al., J. Clin. Invest. 91 (1993) 2791–2795].

On account of their inhibitory action on the protein tyrosine kinase $pp60^{c-src}$, the compounds of the formula I are able to inhibit the bone resorption capability of the osteoclasts. This can be demonstrated, for example, in the so-called bone slice assay on cortical bone slices from cattle using rat osteoclasts in concentrations between about 0.001 and about 10 $\mu$M [the bone slice assay is described, for example, in Biochem. Biophys. Res. Comm. 188 (1992) 1097–1103]. The compounds of the formula I at the same time inhibit the formation of characteristic resorption holes on bone slices in vitro.

In vivo, the activity of the compounds of the formula I can be demonstrated, for example, in the Hock model in the rat. In this test, the compounds of the formula I—on a single oral administration per day in concentrations between about 1 and about 100 mg/kg of body weight—completely or at least partially inhibit for 3–4 weeks the bone loss which is produced in rats by ovariectomy [the "Hock model" is described, for example, in Metab. Bone Dis. 5 (1984) 177–181).

The compounds of the formula I are therefore very highly suitable for the treatment of diseases which respond to inhibition of the activity of the protein tyrosine kinase $pp60^{c-src}$. Osteoporosis, in particular, can be mentioned here, and also other diseases in whose course bone resorption by osteoclasts plays a part, e.g. tumour-induced hypercalcaemia, Paget's Disease or the treatment of bone metastases, and also inflammatory processes in joints and bones and degenerative processes in cartilaginous tissue. Moreover, the compounds of the formula I are useful for the treatment of benign or malignant tumours which respond to inhibition of the protein tyrosine kinase $pp60^{c-src}$, e.g. breast cancer (mammary carcinoma) or bowel cancer (carcinoma of the colon). They are able to cause tumour regression and to prevent tumour metastasization and the growth of micrometastases. The compounds of the formula I are also useful in the treatment of cardiovascular disorders, e.g. thrombosis.

The compounds of the formula I also inhibit the activity of other non-receptor protein tyrosine kinases, e.g. (a) other members of the src family, e.g. lck and fyn, (b) Abl kinase and (c) ZAP70 kinase. Moreover, the compounds of the formula I also inhibit the activity of receptor protein tyrosine kinases, e.g. (a) of the EGF family, e.g. the EGF receptor, c-erbB2, c-erbB3 and c-erbB4, and (b) of the PDGF family, e.g. the PDGF receptor, CSF-1, Kit, VEGF and FGF. On account of these actions, the compounds of the formula I can also be employed for immunomodulation and for the treatment of disorders of the immune system, e.g. in inflammation or organ transplantation. They are furthermore suitable for the treatment of (hyper)proliferative disorders, e.g.

psoriasis, tumours, carcinomas and leukaemias, and in fibrosis and restenosis. The compounds of the formula I can also be used in the treatment of disorders of the central or peripheral nervous system if a signal transmission by at least one protein tyrosine kinase is involved.

The invention relates very particularly to the compounds of the formula 1, in which $R_1$ is phenyl which is unsubstituted or substituted by one or two substituents from the group consisting of lower alkyl, halo-lower alkyl, (hydroxy or lower alkanoyloxy)-lower alkyl, lower alkoxy-lower alkyl, (hydroxy, lower alkoxy or lower alkanoyloxy)-lower alkoxy-lower alkyl, (amino, lower alkylamino, di-lower alkylamino or lower alkanoylamino)-lower alkoxy-lower alkyl, (amino or lower alkanoylamino)-lower alkyl, lower alkylamino-lower alkyl, di-lower alkylamino-lower alkyl, (piperidinyl, piperazinyl, morpholinyl or pyrrolidinyl)-lower alkyl, (imidazolyl, triazolyl, pyridyl, pyrimidinyl or pyrrolyl)-lower alkyl, (hydroxy, lower alkoxy or lower alkanoyloxy)-lower alkylamino-lower alkyl, (amino, lower alkylamino, di-lower alkylamino or lower alkanoylamino)-lower alkylamino-lower alkyl, (piperidinyl, piperazinyl, morpholinyl or pyrrolidinyl)-lower alkylamino-lower alkyl, (imidazolyl, triazolyl, pyridyl, pyrimidinyl or pyrrolyl)-lower alkylamino-lower alkyl, mercapto-lower alkyl, lower alkyl-(thio, sulfinyl or sulfonyl)-lower alkyl, (hydroxy, lower alkoxy or lower alkanoyloxy)-lower alkyl-(thio, sulfinyl or sulfonyl)-lower alkyl, (amino, lower alkylamino, di-lower alkylamino or lower alkanoylamino)-lower alkyl-(thio, sulfinyl or sulfonyl)-lower alkyl, carboxy-lower alkyl, lower alkoxycarbonyl-lower alkyl, aminocarbonyl-lower alkyl, N-lower alkylaminocarbonyl-lower alkyl, N,N-di-lower alkylaminocarbonyl-lower alkyl, hydroxyl, lower alkoxy, lower alkanoyloxy, $C_1$–$C_3$alkylenedioxy, phenyl-lower alkoxy, (hydroxy, lower alkoxy or lower alkanoyloxy)-lower alkoxy, (amino or lower alkanoylamino)-lower alkoxy, lower alkylamino-lower alkoxy, di-lower alkylamino-lower alkoxy, (piperidinyl, piperazinyl, morpholinyl or pyrrolidinyl)-lower alkoxy, (imidazolyl, triazolyl, pyridyl, pyrimidinyl or pyrrolyl)-lower alkoxy, (hydroxy, lower alkoxy or lower alkanoyloxy)-lower alkylamino-lower alkoxy, (amino, lower alkylamino, di-lower alkylamino or lower alkanoylamino)-lower alkylamino-lower alkoxy, (piperidinyl, piperazinyl, morpholinyl or pyrrolidinyl)-lower alkylamino-lower alkoxy, (imidazolyl, triazolyl, pyridyl, pyrimidinyl or pyrrolyl)-lower alkylamino-lower alkoxy, (hydroxy, lower alkoxy or lower alkanoyloxy)-lower alkoxy-lower alkoxy, (amino, lower alkylamino, di-lower alkylamino or lower alkanoylamino)-lower alkoxy-lower alkoxy, (hydroxy, lower alkoxy or lower alkanoyloxy)-lower alkyl-(thio, sulfinyl or sultonyl)-lower alkoxy, (amino, lower alkylamino, di-lower alkylamino or lower alkanoylamino)-lower alkyl-(thio, sulfinyl or sulfonyl)-lower alkoxy, hydroxysulfonyl-lower alkoxy, carboxy-lower alkoxy, lower alkoxycarbonyl-lower alkoxy, aminocarbonyl-lower alkoxy, N-lower alkylaminocarbonyl-lower alkoxy, N,N-di-lower alkylaminocarbonyl-lower alkoxy, amino, lower alkylamino, di-lower alkylamino, lower alkanoylamino, piperidinyl, piperazinyl, morpholinyl, pyrrolidinyl, imidazolyl, triazolyl, pyridyl, pyrimidinyl, pyrrolyl, mercapto, lower alkyl-(thio, sulfinyl or sulfonyl), (hydroxy, lower alkoxy or lower alkanoyloxy)-lower alkyl-(thio, sulfinyl or sulfonyl), (amino, lower alkylamino, di-lower alkylamino or lower alkanoylamino)-lower alkyl-(thio, sulfinyl or sulfonyl), (hydroxy, lower alkoxy or lower alkanoyloxy)-lower alkoxy-lower alkyl-(thio, sulfinyl or sulfonyl), (amino, lower alkylamino, di-lower alkylamino or lower alkanoylamino)-lower alkoxy-lower alkyl-(thio, sulfinyl or sulfonyl), (hydroxy, lower alkoxy or lower alkanoyloxy)-lower alkylamino-lower alkyl-(thio, sulfinyl or sulfonyl), (amino, lower alkylamino, di-lower alkylamino or lower alkanoylamino)-lower alkylamino-lower alkyl-(thio, sulfinyl or sulfonyl), carboxy-lower alkylthio, lower alkoxycarbonyl-lower alkylthio, aminocarbonyl-lower alkylthio, N-lower alkylaminocarbonyl-lower alkylthio, N,N-di-lower alkylaminocarbonyl-lower alkylthio, halogen, carboxyl, lower alkoxycarbonyl, aminocarbonyl, N-lower alkylaminocarbonyl, N-[(hydroxy, lower alkoxy or lower alkanoyloxy)-lower alkyl]-aminocarbonyl, N-[(amino, lower alkylamino, di-lower alkylamino or lower alkanoylamino)-lower alkyl]-aminocarbonyl, N-[(piperidinyl, piperazinyl, morpholinyl or pyrrolidinyl)-lower alkyl]-aminocarbonyl, N-[(imidazolyl, triazolyl, pyridyl, pyrimidinyl or pyrrolyl)-lower alkyl]-aminocarbonyl, N-(hydroxysulfonyl-lower alkyl)-aminocarbonyl, N,N-di-lower alkylaminocarbonyl, cyano, amidino, formamidino and guanidino;

$R_2$ is hydrogen, lower alkyl or halogen; and $R_3$ is phenyl which is unsubstituted or substituted by one, two or three substituents from the group consisting of lower alkyl, hydroxy-lower alkyl, phenyl, hydroxyl, lower alkoxy, phenyl-lower alkoxy, $C_1$–$C_3$alkylenedioxy, cyano and halogen;

with the proviso that $R_3$ is other than phenyl, 4-methoxyphenyl and 4-chlorophenyl if $R_2$ is hydrogen and $R_1$ is phenyl, 4-methylphenyl, 4-methoxyphenyl, 4-chlorophenyl, 4-bromophenyl or 4-iodophenyl;

and salts thereof.

The invention relates primarily to the compounds of the formula I, in which $R_1$ is phenyl which is unsubstituted or substituted by a substituent from the group consisting of lower alkyl, hydroxy-lower alkyl, lower alkanoyloxy-lower alkyl, halo-lower alkyl, amino-lower alkyl, lower alkylamino-lower alkyl, di-lower alkylamino-lower alkyl, (piperidinyl, piperazinyl, morpholinyl or pyrrolidinyl)-lower alkyl, (imidazolyl, triazolyl, pyridyl, pyrimidinyl or pyrrolyl)-lower alkyl, hydroxy-lower alkylamino-lower alkyl, amino-lower alkylamino-lower alkyl, (piperidinyl, piperazinyl, morpholinyl or pyrrolidinyl)-lower alkylamino-lower alkyl, (imidazolyl, triazolyl, pyridyl, pyrimidinyl or pyrrolyl)-lower alkylamino-lower alkyl, mercapto-lower alkyl, lower alkyl-(thio, sulfinyl or sulfonyl)-lower alkyl, hydroxy-lower alkyl-(thio, sulfinyl or sulfonyl)-lower alkyl, amino-lower alkyl-(thio, sulfinyl or sulfonyl)-lower alkyl, hydroxyl, lower alkoxy, $C_1$–$C_3$alkylenedioxy, phenyl-lower alkoxy, hydroxy-lower alkoxy, lower alkoxy-lower alkoxy, lower alkanoyloxy-lower alkoxy, amino-lower alkoxy, lower alkylamino-lower alkoxy, di-lower alkylamino-lower alkoxy, (piperidinyl, piperazinyl, morpholinyl or pyrrolidinyl)-lower alkoxy, (imidazolyl, triazolyl, pyridyl, pyrimidinyl or pyrrolyl)-lower alkoxy, hydroxy-lower alkylamino-lower alkoxy, amino-lower alkylamino-lower alkoxy, (piperidinyl, piperazinyl, morpholinyl or pyrrolidinyl)-lower alkylamino-lower alkoxy, (imidazolyl, triazolyl, pyridyl, pyrimidinyl or pyrrolyl)-lower alkylamino-lower alkoxy, hydroxysulfonyl-lower alkoxy, amino, piperidinyl, piperazinyl, morpholinyl, pyrrolidinyl, imidazolyl, triazolyl, pyridyl, pyrimidinyl, pyrrolyl, mercapto, lower alkyl-(thio, sulfinyl or sulfonyl), hydroxy-lower alkyl-(thio, sulfinyl or sulfonyl), amino-lower alkyl-(thio, sulfinyl or sulfonyl), halogen, carboxyl, lower alkoxycarbonyl, aminocarbonyl, N-lower alkylaminocarbonyl, N-(hydroxy-lower alkyl)-aminocarbonyl, N-(amino-lower alkyl)-aminocarbonyl, N-[(piperidinyl, piperazinyl, morpholinyl or pyrrolidinyl)-lower alkyl]-aminocarbonyl, N-[(imidazolyl, triazolyl, pyridyl, pyrimidinyl or pyrrolyl)-lower alkyl]-aminocarbonyl, N-(hydroxysulfonyl-lower alkyl)-aminocarbonyl, N,N-di-lower alkylaminocarbonyl and cyano;

$R_2$ is hydrogen, lower alkyl or halogen; and $R_3$ is phenyl which is unsubstituted or substituted by one, two or three substituents from the group consisting of lower alkyl, hydroxy-lower alkyl, phenyl, hydroxyl, lower alkoxy, phenyl-lower alkoxy, $C_1$–$C_3$alkylenedioxy, cyano and halogen;

with the proviso that $R_3$ is other than phenyl, 4-methoxyphenyl and 4-chlorophenyl if $R_2$ is hydrogen and $R_1$ is phenyl, 4-methylphenyl, 4-methoxyphenyl, 4-chlorophenyl, 4-bromophenyl or 4-iodophenyl;

and pharmaceutically acceptable salts thereof.

The invention relates in particular to the compounds of the formula I, in which $R_1$ is phenyl which is unsubstituted or substituted by a substituent from the group consisting of lower alkyl, hydroxy-lower alkyl, halo-lower alkyl, amino-lower alkyl, lower alkylamino-lower alkyl, di-lower alkylamino-lower alkyl, (pyrimidinyl, piperazinyl or morpholinyl)-lower alkyl, (imidazolyl, triazolyl, pyridyl or pyrrolyl)-lower alkyl, hydroxy-lower alkylamino-lower alkyl, amino-lower alkylamino-lower alkyl, (pyrimidinyl, piperazinyl or morpholinyl)-lower alkylamino-lower alkyl, (imidazolyl, triazolyl, pyridyl or pyrrolyl)-lower alkylamino-lower alkyl, mercapto-lower alkyl, lower alkyl-(thio, sulfinyl or sulfonyl)-lower alkyl, hydroxy-lower alkyl-(thio, sulfinyl or sulfonyl)-lower alkyl, amino-lower alkyl-(thio, sulfinyl or sulfonyl)-lower alkyl, hydroxyl, lower alkoxy, $C_1$–$C_3$alkylenedioxy, phenyl-lower alkoxy, hydroxy-lower alkoxy, amino-lower alkoxy, lower alkylamino-lower alkoxy, di-lower alkylamino-lower alkoxy, (pyrimidinyl, piperazinyl or morpholinyl)-lower alkoxy, (imidazolyl, triazolyl, pyridyl or pyrrolyl)-lower alkoxy, hydroxy-lower alkylamino-lower alkoxy, amino-lower alkylamino-lower alkoxy, (pyrimidinyl, piperazinyl or morpholinyl)-lower alkylamino-lower alkoxy, (imidazolyl, triazolyl, pyridyl or pyrrolyl)-lower alkylamino-lower alkoxy, hydroxysulfonyl-lower alkoxy, amino, pyrimidinyl, piperazinyl, morpholinyl, imidazolyl, triazolyl, pyridyl, pyrrolyl, mercapto, lower alkyl-(thio, sulfinyl or sulfonyl), hydroxy-lower alkyl-(thio, sulfinyl or sulfonyl), amino-lower alkyl-(thio, sulfinyl or sulfonyl), halogen, carboxyl, lower alkoxycarbonyl, aminocarbonyl, N-lower alkylaminocarbonyl, N-(hydroxy-lower alkyl)-aminocarbonyl, N-(amino-lower alkyl)-aminocarbonyl, N-[(pyrimidinyl, piperazinyl or morpholinyl)-lower alkyl]-aminocarbonyl, N-[(imidazolyl, triazolyl, pyridyl or pyrrolyl)-lower alkyl]-aminocarbonyl, N-(hydroxysulfonyl-lower alkyl)-aminocarbonyl, N,N-di-lower alkylaminocarbonyl and cyano;

$R_2$ is hydrogen, lower alkyl or halogen; and $R_3$ is phenyl which is unsubstituted or substituted by a substituent from the group consisting of lower alkyl, phenyl, hydroxyl, lower alkoxy, phenyl-lower alkoxy, $C_1$–$C_3$alkylenedioxy, cyano and halogen;

with the proviso that $R_3$ is other than phenyl, 4-methoxyphenyl and 4-chlorophenyl if $R_2$ is hydrogen and $R_1$ is phenyl, 4-methylphenyl, 4-methoxyphenyl, 4-chlorophenyl, 4-bromophenyl or 4-iodophenyl;

and pharmaceutically acceptable salts thereof.

Sub-groups of a group of compounds of the formula I which are in each case to be emphasized are:

(a) Compounds of the formula I in which $R_1$ is phenyl which is unsubstituted or monosubstituted in the 3- or 4-position; (b) compounds of the formula I in which $R_1$ is phenyl which is monosubstituted in the 3-position; (c) compounds of the formula I in which $R_1$ is phenyl which is monosubstituted in the 3- or 4-position by 1-imidazolyl-lower alkoxy; (d) compounds of the formula I in which $R_3$ is phenyl which is substituted in the 3- or 4-position by hydroxyl and if desired additionally carries 1 or 2 further substituents selected from amongst lower alkyl, hydroxyl, lower alkoxy and halogen; (e) compounds of the formula I in which $R_3$ is phenyl which is monosubstituted in the 3- or 4-position by hydroxyl; (f) compounds of the formula I in which $R_3$ is phenyl which (1) is monosubstituted in the 3-position by methoxy or chlorine, or (2) is monosubstituted in the 3- or 4-position by lower alkyl, hydroxy-lower alky, phenyl, hydroxyl, $C_2$–$C_7$alkoxy, phenyl-lower alkoxy, cyano, fluorine or bromine, or (3) is di- or trisubstituted by two or three substituents from the group consisting of lower alkyl, hydroxy-lower alkyl, phenyl, hydroxyl, lower alkoxy, phenyl-lower alkoxy, cyano and halogen.

The invention relates especially to the specific compounds and salts thereof described in the examples.

The invention further relates to the use of compounds of the formula I

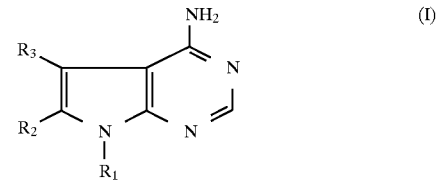

in which $R_1$ is aryl;

$R_2$ is hydrogen, lower alkyl or halogen; and $R_3$ is aryl;

or pharmaceutically acceptable salts thereof, (for the preparation of a medicament) for the treatment of diseases which respond to inhibition of the activity of the protein tyrosine kinase pp60$^{c\text{-}src}$.

The invention preferably relates to the use of those compounds of the formula I in which $R_1$ is phenyl which is unsubstituted or substituted by one or two substituents from the group consisting of lower alkyl, halo-lower alkyl, (hydroxy or lower alkanoyloxy)-lower alkyl, lower alkoxy-lower alkyl, (hydroxy, lower alkoxy or lower alkanoyloxy)-lower alkoxy-lower alkyl, (amino, lower alkylamino, di-lower alkylamino or lower alkanoylamino)-lower alkoxy-lower alkyl, (amino or lower alkanoylamino)-lower alkyl, lower alkylamino-lower alkyl, di-lower alkylamino-lower alkyl, (piperidinyl, piperazinyl, morpholinyl or pyrrolidinyl)-lower alkyl, (imidazolyl, triazolyl, pyridyl, pyrimidinyl or pyrrolyl)-lower alkyl, (hydroxy, lower alkoxy or lower alkanoyloxy)-lower alkylamino-lower alkyl, (amino, lower alkylamino, di-lower alkylamino or lower alkanoylamino)-lower alkylamino-lower alkyl, (piperidinyl, piperazinyl, morpholinyl or pyrrolidinyl)-lower alkylamino-lower alkyl, (imidazolyl, triazolyl, pyridyl, pyrimidinyl or pyrrolyl)-lower alkylamino-lower alkyl, mercapto-lower alkyl, lower alkyl-(thio, sulfinyl or sulfonyl)-lower alkyl, (hydroxy, lower alkoxy or lower alkanoyloxy)-lower alkyl-(thio, sulfinyl or sulfonyl)-lower alkyl, (amino, lower alkylamino, di-lower alkylamino or lower alkanoylamino)-lower alkyl-(thio, sulfinyl or sulfonyl)-lower alkyl, carboxy-lower alkyl, lower alkoxycarbonyl-lower alkyl, aminocarbonyl-lower alkyl, N-lower alkylaminocarbonyl-lower alkyl, N,N-dilower alkylaminocarbonyl-lower alkyl, hydroxyl, lower alkoxy, lower alkanoyloxy, $C_1$–$C_3$alkylenedioxy, phenyl-lower alkoxy, (hydroxy, lower alkoxy or lower alkanoyloxy)-lower alkoxy, (amino or lower alkanoylamino)-lower alkoxy, lower alkylamino-lower alkoxy, di-lower alkylamino-lower alkoxy, (piperidinyl, piperazinyl, morpholinyl or pyrrolidinyl)-lower alkoxy, (imidazolyl, triazolyl, pyridyl, pyrimidinyl or pyrrolyl)-lower alkoxy; (hydroxy, lower alkoxy or lower alkanoyloxy)-lower alkylamino-lower alkoxy, (amino, lower alkylamino, di-lower alkylamino or lower alkanoylamino)-lower alkylamino-lower alkoxy, (piperidinyl, piperazinyl, morpholinyl or pyrrolidinyl)-lower alkylamino-lower alkoxy, (imidazolyl, triazolyl, pyridyl, pyrimidinyl or pyrrolyl)-lower alkylamino-lower alkoxy, (hydroxy, lower alkoxy or lower alkanoyloxy)-lower alkoxy-lower alkoxy, (amino, lower alkylamino, di-lower alkylamino or lower alkanoylamino)-lower alkoxy-lower alkoxy, (hydroxy, lower alkoxy or lower alkanoyloxy)-lower alkyl-(thio, sulfinyl or sulfonyl)-lower alkoxy, (amino, lower alkylamino, di-lower alkylamino or lower alkanoylamino)-lower alkyl-(thio, sulfinyl or sulfonyl)-lower alkoxy, hydroxysulfonyl-lower alkoxy, carboxy-lower alkoxy, lower alkoxycarbonyl-lower alkoxy, aminocarbonyl-lower alkoxy, N-lower alkylaminocarbonyl-lower alkoxy, N,N-di-lower alkylaminocarbonyl-lower alkoxy, amino, lower alkylamino, di-lower alkylamino, lower alkanoylamino, piperidinyl, piperazinyl, morpholinyl, pyrrolidinyl, imidazolyl, triazolyl, pyridyl, pyrimidinyl, pyrrolyl, mercapto, lower alkyl-(thio, sulfinyl or sulfonyl), (hydroxy, lower alkoxy or lower alkanoyloxy)-lower alkyl-(thio, sulfinyl or sulfonyl), (amino, lower alkylamino, di-lower alkylamino or lower alkanoylamino)-lower alkyl-(thio, sulfinyl or sulfonyl), (hydroxy, lower alkoxy or lower alkanoyloxy)-lower alkoxy-lower alkyl-(thio, sulfinyl or sulfonyl), (amino, lower alkylamino, di-lower alkylamino or lower alkanoylamino)-lower alkoxy-lower alkyl-(thio, sulfinyl or sulfonyl), (hydroxy, lower alkoxy or lower alkanoyloxy)-lower alkylamino-lower alkyl-(thio, sulfinyl or sulfonyl), (amino, lower alkylamino, di-lower alkylamino or lower alkanoylamino)-lower alkylamino-lower alkyl-(thio, sulfinyl or sulfonyl), carboxy-lower alkylthio, lower alkoxycarbonyl-lower alkylthio, aminocarbonyl-lower alkylthio, N-lower alkylaminocarbonyl-lower alkylthio, N,N-di-lower alkylaminocarbonyl-lower alkylthio, halogen, carboxyl, lower alkoxycarbonyl, aminocarbonyl, N-lower alkylaminocarbonyl, N-[(hydroxy, lower alkoxy or lower alkanoyloxy)-lower alkyl]-aminocarbonyl, N-[(amino, lower alkylamino, di-lower alkylamino or lower alkanoylamino)-lower alkyl]-aminocarbonyl, N-[(piperidinyl, piperazinyl, morpholinyl or pyrrolidinyl)-lower alkyl]-aminocarbonyl, N-[(imidazolyl, triazolyl, pyridyl, pyrimidinyl or pyrrolyl)-lower alkyl]-aminocarbonyl; N-(hydroxysulfonyl-lower alkyl)-aminocarbonyl, N,N-di-lower alkylaminocarbonyl, cyano, amidino, formamidino and guanidino;

$R_2$ is hydrogen, lower alkyl or halogen; and $R_3$ is phenyl which is unsubstituted or substituted by one, two or three substituents from the group consisting of lower alkyl, hydroxy-lower alkyl, phenyl, hydroxyl, lower alkoxy, phenyl-lower alkoxy, $C_1$–$C_3$alkylenedioxy, cyano and halogen;

or pharmaceutically acceptable salts thereof.

The invention particularly relates to the use of compounds of the formula I in which $R_1$ is phenyl, 4-methylphenyl, 4-methoxyphenyl, 4-chlorophenyl, 4-bromophenyl or 4-iodophenyl, $R_2$ is hydrogen and $R_3$ is phenyl, 4-methoxyphenyl or 4-chlorophenyl, or pharmaceutically acceptable salts thereof.

The compounds of the formula I can be prepared in a manner known per se, for example, by (a) subjecting a compound of the formula II

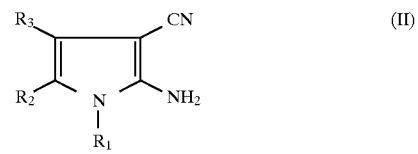

to a ring-closure reaction with synthesis of the pyrimidine ring, or b) subjecting a compound of the formula III

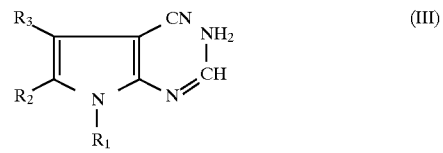

to a ring-closure reaction with synthesis of the pyrimidine ring, or (c) reacting a compound of the formula IV

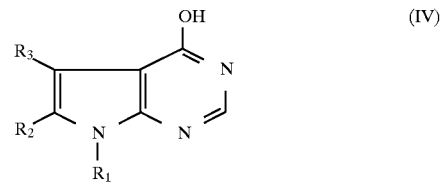

if desired after preliminary activation, with an aminating reagent;

and, if desired, converting a compound of the formula I into another compound of the formula I, and/or, if desired, converting a resulting salt into the free compound or into another salt, and/or, if desired, converting a resulting free compound of the formula I having salt-forming properties into a salt.

In the following more detailed description of the processes, the symbols $R_1$–$R_3$ are each as defined under formula I, if not stated otherwise.

Process (a): The reaction of process (a) corresponds to the cyclization, which is known per se, of 2-amino-3-cyanopyrroles to 4-aminopyrrolo[2,3-d]pyrimidines (see, for example, H. Pichler et al., Liebigs Ann. Chem. 1986, 1485–1505). Possible cyclization reagents are, for example, (1) formamide or (2) 1. trialkyl orthoformate/2. ammonia. The cyclization of the compounds of the formula II with formamide is preferably carried out at elevated temperature, e.g. 160° C., and advantageously with addition of a little DMF and formic acid. The reaction of the compounds of the formula II with trialkyl orthoformates to give the corresponding alkoxyformimidates which are formed as intermediates is normally carried out at less highly elevated temperatures, e.g. 80°–120° C. As a rule, the cyclization of the latter with $NH_3$ is then again carried out at higher temperatures, e.g. at 130° C. in an autoclave.

The compounds of the formula II are preferably prepared using one of the known pyrrole syntheses. They are obtained, for example, by reaction of a compound of the formula IIa

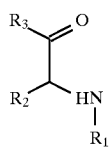

(IIa)

with malononitrile, preferably in the presence of a base, e.g. sodium ethoxide/ethanol.

The compounds of the formula IIa, for their part, can be prepared, for example, by reaction of a compound $R_3$—C(=O)—CH(—$R_2$)-Hal [Hal=halogen], i.e. for example phenacyl bromide or chloride, with a compound $H_2N$—$R_1$, e.g. aniline, preferably in the presence of a base, e.g. sodium carbonate/ethanol or triethylamine/toluene.

Process (b): The ring closure to the corresponding 4-amino-pyrrolo[2,3-d]pyrimidine is carried out, for example, in the presence of suitable bases, e.g. sodium ethoxide/ethanol, preferably at elevated temperature, e.g. 80° C. [see, for example, E. C. Taylor et al., J. Amer. Chem. Soc. 87 (1965)1995–2003].

The amidine compounds of the formula III can be prepared, for example, from the corresponding amino compounds of the formula II according to known amidine syntheses, for example by reaction first with triethyl orthoformate, preferably at elevated temperature, and then with ammonia, preferably at room temperature.

Process (c): Various methods are known for the conversion of 4-hydroxypyrrolo[2,3-d]-pyrimidines into 4-aminopyrrolo[2,3-d]pyrimidines. The compounds of the formula IV can thus be intermediately converted, e.g. by reaction with a halogenating agent, e.g. $PCl_5$ or $POCl_3$, into 4-halo derivatives, which are then reacted further with ammonia. Another method consists in derivatizing the compounds of the formula IV first with a sulfonyl halide, e.g. tosyl, mesyl or trifluoromethylsulfonyl chloride, and then reacting with ammonia.

The compounds of the formula IV can be prepared, for example, from the corresponding compounds of the formula II by ring closure, e.g. with formic acid, preferably at elevated temperature, e.g. 160° C. A further method for the preparation of compounds of the formula IV consists in first cyclizing a compound of the formula IIa with malonic acid mononitrile monoalkyl ester to give the corresponding alkyl pyrrole-3-carboxylate of the formula IVa

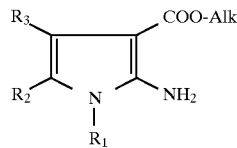

(IVa)

(Alk=alkyl, e.g. ethyl). This is further cyclized, e.g. by reaction with formamide at 160° C., to give the 4-hydroxypyrrolo[2,3-d]pyrimidine of the formula IV.

Compounds of the formula I can be converted into other compounds of the formula I.

Substituents in the aryl radical $R_1$ can thus be converted, for example in a manner known per se, into one another.

Halo-lower alkyl, e.g. chloromethyl, for example, can be reacted according to a nucleophilic substitution reaction, e.g. with substituted or unsubstituted lower alkanols, lower alkanethiols or lower alkylamines, substituted or unsubstituted lower alkoxy-lower alkyl, lower alkylthio-lower alkyl or lower alkylamino-lower alkyl being obtained.

Hydroxyl can be reacted, for example, with substituted or unsubstituted halo-lower alkanes, substituted or unsubstituted lower alkoxy being obtained. Hydroxyl can also be reacted, for example, first with a dihalo-lower alkane, e.g. 1-bromo-2-chloroethane, omega-halo-lower alkoxy being obtained; this can be reacted in an analogous manner as described above with substituted or unsubstituted lower alkanols, lower alkanethiols or lower alkylamines according to a nucleophilic substitution reaction, substituted or unsubstituted lower alkoxy-lower alkoxy, lower alkylthio-lower alkoxy or lower alkylamino-lower alkoxy being obtained.

In an analogous manner to hydroxyl, mercapto can also be alkylated as described in the previous paragraph.

Lower alkylthio groups can be converted into either lower alkylsulfinyl or lower alkylsulfonyl groups by oxidation in a controlled manner.

Amino groups and hydroxyl groups can be acylated in a known manner, lower alkanoylamino and lower alkanoyloxy groups, for example, being obtained.

Carboxylic acid radicals can be converted into carboxylic acid derivatives, for example lower alkoxycarbonyl, aminocarbonyl, N-lower alkylaminocarbonyl, N,N-di-lower alkylaminocarbonyl, cyano or amidino, according to known derivatization methods, for example esterification or amide formation. Conversely, carboxylic acid derivatives can also be converted into free carboxylic acids, e.g. by hydrolysis. Compounds of the formula I in which $R_2$ is hydrogen can be converted into compounds of the formula I in which $R_2$ is halogen by reaction with a halogenating agent, e.g. an N-halosuccinimide.

If any intermediates contain interfering reactive groups, e.g. carboxyl, hydroxyl, mercapto or amino groups, these can be temporarily protected by readily removable protective groups. The choice of suitable protective groups, their introduction and removal are known per se and are described, for example, in J. F. W. McOmie, Protective Groups in Organic Chemistry, Plenum Press, London, New York 1973.

Salts of compounds I can be prepared in a manner known per se. Acid addition salts of compounds I are thus obtained, for example, by treating with a suitable acid or a suitable ion-exchange reagent and salts with bases are obtained by treating with a suitable base or a suitable ion-exchange reagent. Salts of compounds of the formula I can be converted into the free compounds I in a customary manner, acid addition salts can be converted, for example, by treating with a suitable basic agent or a suitable ion-exchange reagent and salts with bases can be converted, for example, by treating with a suitable acid or a suitable ion-exchange reagent.

Salts of compounds I can be converted in a manner known per se into other salts of compounds I, acid addition salts, for example, can be converted into other acid addition salts, e.g. by treating a salt of an inorganic acid, such as a hydrochloride, with a suitable metal salt, such as a sodium, barium or silver salt, of an acid, e.g. with silver acetate, in a suitable solvent in which an inorganic salt formed, e.g. silver chloride, is insoluble and thus separates out from the reaction mixture.

Depending on the procedure and reaction conditions, the compounds I having salt-forming properties can be obtained in free form or in the form of salts.

As a result of the close relationship between the compound I in free form and in the form of its salts, hereinbefore and hereinafter the free compound I or its salts are to be understood analogously and expediently where appropriate as also meaning the corresponding salts or the free compound I.

The compounds I including their salts of salt-forming compounds can also be obtained in the form of their hydrates and/or include other solvents, for example solvents which may be used for the crystallization of compounds existing in solid form.

The compounds I and their salts can exist, depending on the choice of the starting substances and procedures, in the form of one of the possible isomers or as a mixture thereof. In this case, pure diastereomers, for example, are obtainable as pure isomers. Correspondingly, diastereomer mixtures, for example, can exist as isomer mixtures. Isomer mixtures of compounds I in free form or in salt form according to the process or obtainable in other ways can be separated into the components in a customary manner, e.g. in a known manner by fractional crystallization, distillation and/or chromatography on the basis of the physicochemical differences of the constituents. The more active isomer is advantageously isolated.

The invention also relates to those embodiments of the process according to which the starting material used is a compound obtainable in any stage of the process as an intermediate and the missing steps are carried out or a starting substance is used in the form of a derivative or salt or, in particular, formed under the reaction conditions.

In the process of the present invention, those starting substances and intermediates, in each case in free form or in salt form, are preferably used which lead to the compounds I or their salts described as particularly useful at the outset. Novel starting substances and intermediates, in each case in free form or in salt form, for the preparation of the compounds I or their salts, their use and processes for their preparation likewise form a subject of the invention, the variable R being as defined for the compounds I.

The invention likewise relates to the use of the compounds I and their pharmaceutically acceptable salts for the treatment of allergic conditions and disorders, preferably in the form of pharmaceutically acceptable preparations, in particular in a method for the therapeutic treatment of the animal or human body, and to such a treatment method.

The invention likewise relates to pharmaceutical compositions which contain a compound I or a pharmaceutically acceptable salt thereof as active ingredient, and to processes for their preparation. These pharmaceutical compositions are, for example, those for enteral, such as, in particular, oral, and also rectal, administration, those for parenteral administration and those for local administration to warm-blooded mammals, in particular to humans, the pharmacological active ingredient being contained on its own or together with customary pharmaceutical excipients. The pharmaceutical compositions contain (in percentages by weight), for example, from about 0.001% to 100%, preferably from about 0.1% to about 50%, of the active ingredient.

Pharmaceutical compositions for enteral or parenteral administration are, for example, those in unit dose forms, such as sugar coated tablets, tablets, capsules or suppositories, and also ampoules. These are prepared in a manner known per se, e.g. by means of conventional mixing, granulating, sugar coating, dissolving or lyophilizing processes. Pharmaceutical compositions for oral administration can thus be obtained by combining the active ingredient with solid carriers, if desired granulating a mixture obtained and processing the mixture or granules, if desired or necessary, after addition of suitable excipients, to give tablets or sugar coated tablet cores.

Suitable carriers are, in particular, fillers, such as sugars, e.g. lactose, sucrose, mannitol or sorbitol, cellulose preparations and/or calcium phosphates, e.g. tricalcium phosphate or calcium hydrogen phosphate, and also binders, such as starch pastes, using, for example, maize, wheat, rice or potato starch, gelatin, tragacanth, methylcellulose and/or polyvinylpyrrolidone, and, if desired, disintegrants, such as the abovementioned starches, and also carboxymethyl starch, crosslinked polyvinylpyrrolidone, agar or alginic acid or a salt thereof, such as sodium alginate. Excipients are primarily flow regulators and lubricants, e.g. salicylic acid, talc, stearic acid or salts thereof, such as magnesium or calcium stearate, and/or polyethylene glycol. Sugar coated tablet cores are provided with suitable, if desired enteric, coatings, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of enteric coatings, solutions of suitable cellulose preparations, such as acetylcellulose phthalate or hydroxypropylmethylcellulose phthalate. Colorants or pigments, e.g. for the identification or for the characterization of various doses of active ingredients, can be added to the tablets or sugar coated tablet coatings.

Other orally administerable pharmaceutical preparations are hard gelatin capsules and soft, sealed capsules made of gelatin and a softener, such as glycerol or sorbitol. The hard capsules can contain the active compound in the form of granules, e.g. in a mixture with fillers, such as lactose, binders, such as starches, and/or lubricants, such as talc or magnesium stearate, and, if desired, stabilizers. In soft capsules, the active ingredient is preferably dissolved or suspended in suitable liquids, such as fatty oils, liquid paraffin or liquid polyethylene glycols, it likewise being possible to add stabilizers.

Suitable rectally administerable pharmaceutical compositions are, for example, suppositories which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules can also be used which contain a combination of the active compound with a base substance. Possible base substances are, for example, liquid triglycerides, polyethylene glycols or paraffin hydrocarbons.

For parenteral administration, aqueous solutions of an active ingredient in water-soluble form, e.g. of a water-soluble salt, are primarily suitable, and also suspensions of the active ingredient, such as appropriate oily injection suspensions, suitable lipophilic solvents or vehicles, such as fatty oils, e.g. sesame oil, or synthetic fatty acid esters, e.g. ethyl oleate or triglycerides, being used, or aqueous injection suspensions which contain viscosity-increasing substances, e.g. sodium carboxymethylcellulose, sorbitol and/or dextran, and, if desired, also stabilizers.

Pharmaceutical compositions for local administration are, for example, lotions, creams and ointments for the topical treatment of the skin, i.e. liquid or semi-solid oil-in-water or water-in-oil emulsions, fatty ointments which are water-free, pastes, i.e. creams and ointments containing secretion-absorbing powder constituents, gels which are aqueous, low in water or water-free and consist of swellable, gel-forming materials, foams, i.e. liquid oil-in-water emulsions present in aerosol form, which are administered from pressure containers, and tinctures containing an aqueous-ethanolic base, which in each case can contain other customary pharmaceutical excipients, such as preservatives. The pharmaceutical compositions for local administration are prepared in a manner known per se by mixing the active ingredient with the pharmaceutical excipients, e.g. by dissolving or suspending the active ingredient in the base or in a part thereof, if necessary. For the preparation of emulsions in which the active ingredient is dissolved in one of the liquid phases, as a rule the active ingredient is dissolved in this before emulsification; for the preparation of suspensions in which the active ingredient is suspended in the emulsion, the active ingredient is mixed with a part of the base after emulsification and the rest of the formulation is then added.

The dose of the active ingredient can depend on various factors, such as efficacy and duration of efficacy of the active ingredient, severity of the disease to be treated or its symptoms, administration procedure, warm-blooded animal species, sex, age, weight and/or individual condition of the warm-blooded animal. In the normal case, for a warm-blooded animal of about 75 kg in weight one, e.g. oral, daily dose of about 1 mg to about 1000 mg, in particular from about 5 to about 200 mg, is to be estimated. This can be administered, for example, as a single dose or in several sub-doses, e.g. those from 10 to 100 mg.

The following examples illustrate the invention described above. Temperatures are given in degrees Celsius; ether=diethyl ether, EA=ethyl acetate; THF=tetrahydrofuran; DMF=N,N-dimethylformamide; hexane means an isomer mixture of various hexanes (Fluka), RE=rotary evaporator; RT=room temperature; HV=high vacuum; h=hour(s).

REFERENCE EXAMPLE 1

5,7-Diphenyl-4-aminopyrrolo[2,3-d]pyrimidine 20 g of 1,4-diphenyl-2-amino-3-cyanopyrrole are heated under reflux for 2.5 h in 400 ml of ethyl orthoformate and 2 ml of acetic anhydride. The mixture is then concentrated in an RE and the residue is crystallized from ether/petroleum ether. 1,4-Diphenyl-2-(N-ethoxy-formimidato)-3-cyanopyrrole having a melting point of 90°–92° C. is obtained.

18 g of 1,4-diphenyl-2-(N-ethoxyformimidato)-3-cyanopyrrole are dissolved in 150 ml of warm ethanol and the solution is treated at RT with 250 ml of ammonia in ethanol (8%) and allowed to stand overnight. The solid formed is filtered and dried, 1,4-diphenyl- 2-(N-formamidino)-3-cyanopyrrole having a melting point of 195° C. being obtained. The mother liquor is concentrated to two-thirds, cooled to 0° C. and filtered, further 1,4-diphenyl-2-(N-formamidino)-3-cyanopyrrole having a melting point of 195° C. being obtained.

500 ml of ammonia in 8% ethanol and 14 g of 1,4-diphenyl-2-(N-formamidino)-3-cyanopyrrole are heated at 130° C. for 4 h in an autoclave. After cooling to RT, the precipitated product is filtered off. The mother liquor is concentrated to two-thirds and cooled to 0° C. and filtered, further product being obtained. The product is dissolved hot in ethanol/chloroform, and the solution is treated with active carbon and filtered. The chloroform is slowly stripped off in an RE, pure 5,7-diphenyl-4-aminopyrrolo[2,3-d]pyrimidine crystallizing out. After filtration and drying under HV, 5,7-diphenyl-4-aminopyrrolo[2,3-d]pyrimidine having a melting point of 200°–201° C. is obtained. $^1$H—NMR (CDCl$_3$): delta (ppm)=5.4 (br. s, 2H), 7.3–7.6 (m, 9H), 7.8 (d, 2H), 8.35 (s, 1H).

(a) 1,4-Diphenyl-2-amino-3-cyanopyrrole:

3 g of sodium are dissolved in 300 ml of ethanol and subsequently first 7.6 g of malononitrile and then 20 g of 2'-(phenylamino)acetophenone are added at RT and the mixture is heated at 80° C. for 1.25 h. The mixture is then treated hot with water until it becomes cloudy and cooled, the product crystallizing out. After filtration and drying under HV, 1,4-diphenyl-2-amino-3-cyanopyrrole having a melting point of 135° C. is obtained.

(b) 2'-Phenylaminoacetophenone:

40 g of phenacyl bromide and 20 ml of aniline are stirred at 70° C. for 3 h in 500 ml of ethanol in the presence of 80 g of powdered Na$_2$CO$_3$. The mixture is cooled, treated with water and filtered. The crystals are dissolved in methylene chloride, then washed with water, dried over MgSO$_4$ and concentrated to two-thirds. After addition of petroleum ether the product crystallizes out and, after filtration and drying under HV, 2'-(phenylamino)acetophenone having a melting point of 95° C. is obtained.

EXAMPLE 2

5,7-Diphenyl-6-methyl-4-amino-pyrrolo[2,3-d]pyrimidine 0.8 g of 1,4-diphenyl-5-methyl-2-amino-3-cyanopyrrole is heated at 190° C. for 2.5 h under a nitrogen atmosphere in 1 ml of formamide. After cooling to RT, the mixture is dissolved in a little methylene chloride and chromatographed on silica gel (methylene chloride/methanol 20:1). After crystallization from ether, 5,7-diphenyl-6-methyl-4-aminopyrrolo[2,3-d]pyrimidine having a melting point of 170°–172° C. is obtained. $^1$H—NMR (CDCl3): delta (ppm) =2.2 (s, 3H), 5.1 (br. s, 2H), 7.3–7.6 (m, 10H), 8.3 (s, 1H).

(a) 1,4-Diphenyl-5-methyl-2-amino-3-cyanopyrrole:

0.5 g of sodium is dissolved in 100 ml of ethanol and subsequently first 1.6 g of malononitrile and then 5 g of 2'-(phenylamino)-propiophenone are added at RT and the mixture is boiled under reflux for 20 h. The mixture is then cooled and concentrated in an RE. The residue is partitioned between water and methylene chloride and the aqueous phase is extracted once more with methylene chloride. The combined organic phases are dried over MgSO$_4$ and concentrated. The product is dissolved in ether, filtered and crystallized by addition of petroleum ether. After filtration and drying under HV, 1,4-diphenyl-5-methyl-2-amino-3-cyanopyrrole having a melting point of 150° C. is obtained.

(b) 2'-Phenylaminopropiophenone:

15 ml of 2'-bromopropiophenone and 9.5 ml of aniline are stirred at 55° C. for 20 h in 200 ml of toluene in the presence of 14 ml of triethylamine. The mixture is cooled, treated with water and extracted. The organic phase is dried over MgSO$_4$ and concentrated. The product is dissolved in petroleum ether, filtered and crystallized by cooling to 0° C. After filtration and drying under HV, 2'-(phenylamino) propiophenone having a melting point of 97°–99° C. is obtained.

EXAMPLE 3

5-(2-Chlorophenyl)-7-phenyl-4-aminopyrrolo[2,3-d]pyrimidine 4 g of 4-(2-chlorophenyl)-1-phenyl-2-amino-3-cyanopyrrole are heated at 190° C. with a spatula tipful of dimethylaminopyridine for 3.5 h under a nitrogen atmosphere in 50 ml of formamide. After cooling to RT, the mixture is treated with water and extracted 3 times with ethyl acetate. The organic phases are washed with water, dried over MgSO$_4$ and concentrated. After chromatography on silica gel (methylene chloride/methanol 14:1) and crystallization from ethyl acetate/ether, 5-(2-chlorophenyl)-7-phenyl-4-amino-pyrrolo-[2,3-d]pyrimidine having a melting point of 175°–176° C. is obtained. $^1$H—NMR (CDCl$_3$): delta (ppm)=4.9 (br. s, 2H), 7.3 (s, 1H), 7.35–7.45 (m, 3H), 7.45–7.6 (m, 4H), 7.75 (d, 2H), 8.4 (s, 1H).

(a) 4-(2-Chlorophenyl)-1-phenyl-2-amino-3-cyanopyrrole:

4.0 g of potassium tertiary butoxide are dissolved in 80 ml of ethanol and subsequently first 3.0 g of malononitrile and then 9 g of 2'-phenylamino-2-chloroacetophenone are added at RT and the mixture is stirred at 65° C. for 2 h. The mixture is then cooled and concentrated in an RE. The residue is partitioned between water and methylene chloride and the aqueous phase is extracted once more with methylene chloride. The combined organic phases are dried over MgSO$_4$ and concentrated. The product is chromatographed on silica gel using methylene chloride and the product-containing fractions are concentrated, 4-(2-chlorophenyl)-1-phenyl-2-amino-3-cyanopyrrole being obtained as a reddish, viscous oil which is directly further processed.

(b) 2'-Phenylamino-2-chloroacetophenone:

8 g of 2'-bromo-2-chloroacetophenone and 2.6 g of aniline are stirred at 60° C. for 2.5 h in 100 ml of ethanol in the presence of 8 g of powdered $Na_2CO_3$. The mixture is then cooled and concentrated in an RE. The residue is partitioned between water and methylene chloride and the aqueous phase is extracted once more with methylene chloride. The combined organic phases are dried over $MgSO_4$ and concentrated. The oily product is employed in the next stage without further purification.

(c) 2'-Bromo-2-chloroacetophenone:

15.2 g of copper(II) bromide ($CuBr_2$) are initially introduced in 45 ml of EA and heated to 60° C. with stirring. 5.0 g of 2-chloroacetophenone in 45 ml of chloroform are then added dropwise during the course of 0.5 h and the mixture is boiled under reflux for 2.5 h. After cooling to RT, the suspension is filtered and the mother liquor is concentrated in an RE. The oily product is employed in the next stage without further purification.

EXAMPLE 4

5-(3-Chlorophenyl)-7-phenyl-4-aminopyrrolo[2,3-d]pyrimidine 1 g of 4-(3-chlorophenyl)-1-phenyl-2-amino-3-cyanopyrrole is heated at 180° C. with a spatula tipful of dimethylaminopyridine for 14 h in 10 ml of formamide under a nitrogen atmosphere. After cooling to RT, the mixture is treated with water and the crystals obtained are filtered off, washed with water and dried. After chromatography on silica gel (methylene chloride/methanol 15:1), the product-containing fractions are concentrated, slurried in ether and filtered. 5-(3-Chlorophenyl)-7-phenyl-4-aminopyrrolo[2,3-d]pyrimidine having a melting point of 173°–175° C. is obtained. $^1$H—NMR ($d_6$-DMSO): delta (ppm)=6.3 (br. s, 2H), 7.3–7.55 (m, 6H), 7.65(s, 1H), 7.8 (s, 1H), 7.85 (d, 2H), 8.2 (s, 1H).

(a) 4-(3-Chlorophenyl)-1-phenyl-2-amino-3-cyanopyrrole:

0.24 g of sodium is dissolved in 40 ml of ethanol and subsequently first 0.76 g of malononitrile and then 2.37 g of 2'-phenyl-amino-3-chloroacetophenone are added at RT and the mixture is stirred at 50° C. for 1.5 h. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether/petroleum ether and the crystals are filtered off, 4-(3-chloro-phenyl)-1-phenyl-2-amino-3-cyanopyrrole being obtained. Further product is analogously obtained again from the mother liquor.

(b) 2'-Phenylamino-3-chloroacetophenone:

3.5 g of 2'-bromo-3-chloroacetophenone and 1.53 g of aniline are stirred at 50° C. for 1.5 h in 40 ml of ethanol in the presence of 3.5 g of powdered $Na_2CO_3$. The mixture is then cooled and concentrated in an RE. The residue is partitioned between water and methylene chloride and the aqueous phase is extracted twice with methylene chloride. The residue is slurried with ether/petroleum ether and the crystals are filtered off, 2'-phenylamino-3-chloroacetophenone being obtained.

(c) 2'-Bromo-3-chloroacetophenone:

Analogously to Example 3, starting from 3-chloroacetophenone, after boiling under reflux for 4 h, the oily product 2'-bromo-3-chloroacetophenone is obtained, which is employed without further purification in the next stage.

EXAMPLE 5

5-(3-Methoxyphenyl)-7-phenyl-4-aminopyrrolo[2,3-d]pyrimidine 1.27 g of 4-(3-methoxyphenyl)-1-phenyl-2-amino-3-cyanopyrrole are heated at 180° C. with a spatula tipful of dimethylaminopyridine for 7 h in 14 ml of formamide under a nitrogen atmosphere. After cooling to RT, the mixture is treated with water and the crystals obtained are filtered off, washed with water and dried. After chromatography on silica gel (ethyl acetate/hexane 4:1), the product-containing fractions are concentrated, slurried in ether and filtered. 5-(3-Methoxyphenyl)-7-phenyl-4-aminopyrrolo[2,3-d]pyrimidine having a melting point of 159°–160° C. is obtained. $^1$H—NMR ($d_6$-DMSO): delta (ppm)=3.8 (s, 3H), 6.3 (br. s, 2H), 6.9 (br. d, 1H), 7.1 (m, 2H), 7.3–7.45 (m, 2H), 7.55(t, 2H), 7.75 (s, 1H), 7.9 (d, 2H), 8.2 (s, 1H).

(a) 4-(3-Methoxyphenyl)-1-phenyl-2-amino-3-cyanopyrrole:

0.12 g of sodium is dissolved in 20 ml of ethanol and subsequently first 0.32 g of malononitrile and then 1.06 g of 2'-phenylamino-3-methoxyacetophenone are added at RT and the mixture is stirred at 50° C. for 2.5 h. The mixture is then cooled and concentrated in an RE. The residue is partitioned between water and EA and the aqueous phase is extracted twice with EA. The combined organic phases are dried over $Na_2SO_4$ and concentrated. The oily product 4-(3-methoxy-phenyl)-1-phenyl-2-amino-3-cyanopyrrole is employed in the next stage without further purification.

(b) 2'-Phenylamino-3-methoxyacetophenone:

2 g of 3-methoxyphenacyl bromide and 0.89 g of aniline are stirred at 50° C. for 1.5 h in 20 ml of ethanol in the presence of 2.0 g of powdered $Na_2CO_3$. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether/petroleum ether and the crystals are filtered off, 2'-phenylamino-3-methoxyacetophenone being obtained. Further product is analogously obtained again from the mother liquor.

EXAMPLE 6

5-(4-Fluorophenyl)-7-phenyl-4-amino-pyrrolo[2,3-d]pyrimidine 4.78 g of 4-(4-fluorophenyl)-1-phenyl-2-amino-3-cyanopyrrole are heated at 180° C. with a spatula tipful of dimethylaminopyridine for 3.5 h in 50 ml of formamide under a nitrogen atmosphere. After cooling to RT, the mixture is treated with water and extracted 3 times with EA. The organic phases are washed with water, dried over $Na_2SO_4$ and concentrated. The residue is slurried with EA/ether and the crystals are filtered off. The crystals are suspended in hot ethanol and filtered off after cooling to RT. 5-(4-Fluorophenyl)-7-phenyl-4-aminopyrrolo[2,3-d]pyrimidine having a melting point of 202°–203° C. is obtained. $^1$H—NMR ($d_6$-DMSO): delta (ppm)=6.3 (br. s, 2H), 7.3–7.4 (m, 3H), 7.5–7.65 (m, 4H), 7.75 (s, 1H), 7.85 (d, 2H), 8.2 (s,1H).

(a) 4-(4-Fluorophenyl)-1-phenyl-2-amino-3-cyanopyrrole:

0.57 g of sodium is dissolved in 80 ml of ethanol and subsequently first 1.79 g of malononitrile and then 5.17 g of 2'-phenyl-amino-4-fluoroacetophenone are added at RT and the mixture is stirred at 50° C. for 2.5 h. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether/petroleum ether and the crystals are filtered off, 4-(4-fluorophenyl)-1-phenyl-2-amino-3-cyanopyrrole being obtained. Further product is analogously obtained again from the mother liquor.

(b) 2'-(Phenylamino)-4-fluoroacetophenone:

5 g of 4-fluorophenacyl chloride and 3 g of aniline are stirred at 50° C. for 1.75 h in 50 ml of ethanol in the presence of 6.7 g of powdered $Na_2CO_3$ and 0.87 g of NaI. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether and the crystals are filtered, 2'-phenylamino-4-fluoroacetophenone being obtained. Further product is analogously obtained again from the mother liquor after addition of petroleum ether.

EXAMPLE 7

5-(2-Methylphenyl)-7-phenyl-4-aminopyrrolo[2,3-d]pyrimidine 7.1 g of 4-(2-methylphenyl)-1-phenyl-2-amino-3-cyanopyrrole are heated at 160° C. for 8 h in a mixture of 60 ml of formamide, 30 ml of formic acid and 14 ml of dimethylformamide. After cooling to RT, formic acid and DMF are stripped off in an RE and the residue is treated with water, adjusted to neutrality and extracted 3 times with methylene chloride. The organic phases are washed with water, dried over $Na_2SO_4$ and concentrated. After chromatography on silica gel (EA/hexane 4:1), the product-containing fractions are concentrated, slurried in ether and filtered. 5-(2-Methylphenyl)-7-phenyl-4-aminopyrrolo[2,3-d]pyrimidine having a melting point of 181°–182° C. is obtained. $^1$H—NMR ($d_6$-DMSO): delta (ppm)=2.25 (s, 3H), 6.8 (br. s, 2H), 7.3–7.4 (m, 5H), 7.55 (m, 2H), 7.65 (s, 1H), 7.9 (d, 2H), 8.2 (s, 1H).

(a) 4-(2-Methylphenyl)-1-phenyl-2-amino-3-cyanopyrrole:

0.83 g of sodium is dissolved in 80 ml of ethanol and subsequently first 2.61 g of malononitrile and then 7.4 g of 2'-phenylamino-2-methylacetophenone are added at RT and the mixture is stirred at 50° C. for 4 h. The mixture is then cooled and concentrated in an RE. The residue is partitioned between water and methylene chloride and the aqueous phase is extracted twice with methylene chloride. The combined organic phases are dried over $Na_2SO_4$ and concentrated. The oily product 4-(2-methylphenyl)-1-phenyl-2-amino-3-cyanopyrrole is employed in the next stage without further purification.

(b) 2'-Phenylamino-2-methylacetophenone:

8.0 g of 2-methylphenacyl bromide and 3.3 ml of aniline are stirred at 50° C. for 3 h in 80 ml of ethanol in the presence of 7.67 g of powdered $Na_2CO_3$. The mixture is then cooled and concentrated in an RE. The residue is partitioned between water and methylene chloride and the aqueous phase is extracted twice with methylene chloride. The combined organic phases are dried over $Na_2SO_4$ and concentrated. The oily product 2'-phenylamino-2-methylacetophenone is employed in the next step without further purification.

(c) 2'-Bromo-2-methylacetophenone:

Analogously to Example 3, starting from 2-methylacetophenone the oily product 2'-bromo-2-methylacetophenone is obtained, which is employed in the next stage without further purification. [35.0 g of copper(II) bromide ($CuBr_2$) are initially introduced in 90 ml of EA and the mixture is heated to 60° C. with stirring. 10.0 g of 2-methylacetophenone in 90 ml of chloroform are then added dropwise during the course of 0.75 h and the mixture is boiled under reflux for 1.5 h. After cooling to RT, the suspension is filtered and the mother liquor concentrated in an RE. The oily product is employed in the next stage without further purification].

EXAMPLE 8

5,7-Bis(4-fluorophenyl)-4-aminopyrrolo[2,3-d]pyrimidine 3.6 g of 1,4-bis(4-fluorophenyl)-2-amino-3-cyanopyrrole and 0.6 ml of acetic anhydride are boiled under reflux for 2.5 h in 50 ml of triethyl orthoformate. After cooling to RT, the mixture is treated with hexane and cooled to 0° C., and the crystals are filtered off and washed with hexane. 1,4-Bis(4-fluorophenyl)-2-(N-ethoxyformimidato)-3-cyanopyrrole is obtained.

150 ml of ammonia in ethanol (about 8%) and 3.65 g of 1,4-bis(4-fluorophenyl)-2-(N-ethoxyformimidato)-3-cyanopyrrole are heated at 130° C. for 5 h in an autoclave. After cooling to RT, the mixture is concentrated to ¾ and the residue is treated with ether. The precipitated product is filtered off and washed with ether. After filtration and drying under HV, 5,7-bis(4-fluorophenyl)-4-aminopyrrolo[2,3-d]pyrimidine having a melting point of 253°–254° C. is obtained. $^1$H—NMR ($d_6$-DMSO): delta (ppm)=$^1$H—NMR: 6.3 (br. s, 2H), 7.3–7.4 (m, 4H), 7.5–7.65 (m, 2H), 7.7 (s, 1H), 7.9 (m, 2H), 8.2 (s, 1H).

(a) 1,4-Bis(4-fluorophenyl)-2-amino-3-cyanopyrrole:

0.56 g of sodium is dissolved in 90 ml of ethanol and subsequently first 1.75 g of malononitrile and then 5.48 g of 2'-(4-fluorophenylamino)-4-fluoroacetophenone are added at RT and the mixture is stirred at 50° C. for 1.5 h. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether/petroleum ether and the crystals are filtered off, 1,4-bis(4-fluorophenyl)-2-amino-3-cyanopyrrole being obtained. Further product is analogously obtained again from the mother liquor.

(b) 2'-(4-Fluorophenylamino)-4-fluoroacetophenone:

5 g of 4-fluorophenacyl chloride and 3.54 g of 4-fluoroaniline are stirred at 50° C. for 1.5 h in 50 ml of ethanol in the presence of 6.7 g of powdered $Na_2CO_3$ and 0.87 g of NaI. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether/petroleum ether and the crystals are filtered off, 2'-(4-fluorophenylamino)-4-fluoroacetophenone being obtained. Further product is again obtained from the mother liquor after addition of petroleum ether.

EXAMPLE 9

5-Phenyl-7-(3-ethoxyphenyl)-4-aminopyrrolo[2,3-d]pyrimidine 4.75 g of 4-phenyl-1-(3-ethoxyphenyl)-2-amino-3-cyanopyrrole and 0.8 ml of acetic anhydride are boiled under reflux for 1.5 h in 60 ml of triethyl orthoformate. After cooling to RT, the mixture is concentrated in an RE. After chromatography of the oil on silica gel (methylene chloride/hexane 3:2), the product-containing fractions are concentrated. 4-Phenyl-1-(3-ethoxyphenyl)-2-(N-ethoxyformimidato)-3-cyanopyrrole is obtained in crystalline form.

160 ml of ammonia in ethanol (about 8%) and 4.28 g of 4-phenyl-1-(3-ethoxyphenyl)-2-(N-ethoxyformimidato)-3-cyanopyrrole are heated at 130° C. for 6.5 h in an autoclave. After cooling to RT, the mixture is concentrated. After chromatography of the oil on silica gel (methylene chloride/methanol 95:5), the product-containing fractions are concentrated. The residue is slurried with ether and the crystals are filtered off. After filtration and drying under HV, 5-phenyl-7-(3-ethoxyphenyl)-4-aminopyrrolo[2,3-d]pyrimidine having a melting point of 138°–139° C. is obtained. $^1$H—NMR (d$_6$-DMSO): delta (ppm)=1.35 (t, 3H), 4.1 (q, 2H), 6.2 (br. s, 2H), 6.9 (br. d, 1H), 7.35–7.6 (m, 9H), 7.75 (s, 1H), 8.2 (s, 1H).

(a) 4-Phenyl-1-(3-ethoxyphenyl)-2-amino-3-cyanopyrrole:

0.4 g of sodium is dissolved in 70 ml of ethanol and subsequently first 1.24 g of malononitrile and then 4.0 g of 2'-(3-ethoxyphenylamino)acetophenone are added at RT and the mixture is stirred at 50° C. for 2 h. The mixture is then cooled and concentrated in an RE. The residue is partitioned between water and methylene chloride and the aqueous phase is extracted twice with methylene chloride. The combined organic phases are dried over Na$_2$SO$_4$ and concentrated, 4-phenyl-1-(3-ethoxyphenyl)-2-amino-3-cyanopyrrole being obtained. The oily product is employed in the next stage without further purification.

(b) 2'-(3-Ethoxyphenylamino)acetophenone:

5 g of phenacyl bromide and 3.78 g of m-phenetidine are stirred at 50° C. for 2.5 h in 50 ml of ethanol in the presence of 5.85 g of powdered Na$_2$CO$_3$. The mixture is then cooled and concentrated in an RE. The residue is partitioned between water and methylene chloride and the aqueous phase is extracted twice with methylene chloride. The combined organic phases are dried over Na$_2$SO$_4$ and concentrated. The residue is slurried with ether and the crystals are filtered off, 2'-(3-ethoxyphenylamino)acetophenone being obtained. Further product is again obtained from the mother liquor after addition of petroleum ether.

EXAMPLE 10

5-(3,5-Dimethoxyphenyl)-7-phenyl-4-amino-pyrrolo[2,3-d]pyrimidine 1.81 g of 4-(3,5-dimethoxyphenyl-1-phenyl-2-amino-3-cyanopyrrole and 0.3 ml of acetic anhydride are boiled under reflux for 2 h in 25 ml of triethyl orthoformate. After cooling to RT, the mixture is concentrated in an RE. 4-(3,5-dimethoxyphenyl)-1-phenyl-2-(N-ethoxy-formimidato)-3-cyanopyrrole is obtained as a brownish oil.

120 ml of ammonia in ethanol (about 8%) and 4.28 g of 4-(3,5-dimethoxyphenyl)-1-phenyl-2-(N-ethoxyformimidato)-3-cyanopyrrole are heated at 130° C. for 3.5 h in an autoclave. After cooling to RT, the mixture is concentrated. The residue is treated with ether and the precipitated product is filtered off. The crystals are dissolved in hot ethanol/methylene chloride, and the solution is treated with active carbon, filtered and concentrated to ⅔ in an RE. After cooling to 0° C., the crystals formed are filtered off. After drying under HV, 5-(3,5-dimethoxyphenyl)-7-phenyl-4-aminopyrrolo[2,3-d]pyrimidine having a melting point of 211°–212° C. is obtained. $^1$H—NMR (d$_6$-DMSO): delta (ppm)=3.8 (s, 6H), 6.3 (br. s, 2H), 6.5 (br. s, 1H), 6.7 (br. s, 2H), 7.35 (m, 1H), 7.55 (m, 2H), 7.75 (s, 1H), 7.9 (d, 2H), 8.2 (s, 1H).

(a) 4-(3,5-Dimethoxyphenyl)-1-phenyl-2-amino-3-cyanopyrrole:

0.14 g of sodium is dissolved in 25 ml of ethanol and subsequently first 0.45 g of malononitrile and then 1.54 g of 2'-phenylamino-3,5-dimethoxyacetophenone are added at RT and the mixture is stirred at 50° C. for 1.5 h. The mixture is then cooled and concentrated in an RE. The residue is partitioned between water and methylene chloride and the aqueous phase is extracted twice with methylene chloride. The combined organic phases are dried over Na$_2$SO$_4$ and concentrated. The oily product 4-(3,5-dimethoxyphenyl)-1-phenyl-2-amino-3-cyanopyrrole is employed in the next stage without further purification.

(b) 2'-(Phenylamino)-3,5-dimethoxyacetophenone:

8.0 g of 2'-bromo-3,5-dimethoxyacetophenone and 1.54 ml of aniline are stirred at 50° C. for 1.5 h in 40 ml of ethanol in the presence of 3.59 g of powdered Na$_2$CO$_3$. The mixture is then cooled and concentrated in an RE. The residue is partitioned between water and methylene chloride and the aqueous phase is extracted twice with methylene chloride. The combined organic phases are dried over Na$_2$SO$_4$ and concentrated. The residue is taken up in a little ether and allowed to stand at 0° C. for three days. The crystals are filtered off, washed with ether and dried under HV. 2'-Phenylamino-3,5-dimethoxyacetophenone is obtained.

(c) 2'-Bromo-3,5-dimethoxyacetophenone:

Similarly to Example 3, starting from 3,5-dimethoxyacetophenone the oily product 2'-bromo-3,5-dimethoxyacetophenone is obtained, which is employed in the next stage without further purification.

EXAMPLE 11

5-Phenyl-7-(3-benzyloxyphenyl)-4-aminopyrrolo[2,3-d]pyrimidine 13.76 g of 4-phenyl-1-(3-benzyloxyphenyl)-2-amino-3-cyanopyrrole and 2.3 ml of acetic anhydride are boiled under reflux for 1.5 h in 170 ml of triethyl orthoformate. After cooling to RT, the mixture is concentrated in an RE. After chromatography of the oil on silica gel (methylene chloride/hexane 3:2), the product-containing fractions are concentrated. 4-Phenyl-1-(3-benzyloxyphenyl)-2-(N-ethoxyformimidato)-3-cyanopyrrole is obtained in crystalline form.

350 ml of ammonia in ethanol (about 8%) and 4.28 g of 4-phenyl-1-(3-ethoxyphenyl)-2-(N-ethoxyformimidato)-3-cyanopyrrole are heated at 130° C. for 5 h in an autoclave. After cooling to RT, the mixture is concentrated. After chromatography of the oil on silica gel (methylene chloride/methanol 95:5), the product-containing fractions are concentrated. The residue is slurried with ether and the crystals are filtered off. After filtration and drying under HV, 5-phenyl-7-(3-ethoxyphenyl)-4-aminopyrrolo[2,3-d]pyrimidine having a melting point of 141°–142° C. is obtained. 4-Phenyl-1-(3-ethoxyphenyl)-2-(N-formamidino)-3-cyanopyrrole is obtained as a by-product, which can likewise be cyclized to 5-phenyl-7-(3-ethoxyphenyl)-4-aminopyrrolo[2,3-d]pyrimidine at 160° C. analogously to Example 7 in formamide, formic acid and DMF. $^1$H—NMR (d$_6$-DMSO): delta (ppm)=5.2 (s, 2H), 6.2 (br. s, 2H), 7.0 (br. d, 1H), 7.3–7.65 (m, 13H), 7.75 (s, 1H), 8.2 (s, 1H).

(a) 4-Phenyl-1-(3-benzyloxyphenyl)-2-amino-3-cyanopyrrole:

0.95 g of sodium is dissolved in 200 ml of ethanol and subsequently first 2.98 g of malononitrile and then 11.96 g of 2'-(3-benzyloxyphenylamino)acetophenone are added at RT and the mixture is stirred at 50° C. for 2 h. The mixture is then cooled and concentrated in an RE. The residue is partitioned between water and methylene chloride and the aqueous phase is extracted twice with methylene chloride. The combined organic phases are dried over Na$_2$SO$_4$ and concentrated, 4-phenyl-1-(3-benzyloxyphenyl)-2-amino-3-cyanopyrrole being obtained. The oily product is employed in the next stage without further purification.

(b) 2'-(3-Benzyloxyphenylamino)acetophenone:

10 g of phenacyl bromide and 11 g of 3-benzyloxyaniline are stirred at 60° C. for 2 h in 100 ml of ethanol in the presence of 11.7 g of powdered Na$_2$CO$_3$. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether and the crystals are filtered off, 2'-(3-benzyloxyphenylamino)acetophenone being obtained.

EXAMPLE 12

5-Phenyl-7-(3-hydroxyphenyl)-4-aminopyrrolo[2,3-d]pyrimidine 2.61 g of 5-phenyl-7-(3-benzyloxyphenyl)-4-aminopyrrolo[2,3-d]pyrimidine (Ex. 11) and 1.0 g of palladium on carbon 10% are stirred at 40° C. for 30 h in 100 ml of THF until the amount of hydrogen theoretically required has been consumed. After cooling to RT, the mixture is filtered and the filtrate is concentrated in an RE. The residue is slurried with ether and the crystals are filtered off. Recrystallization from methylene chloride/ethanol and from chloroform does not give a pure product. After chromatography on silica gel (methylene chloride/methanol containing $NH_3$ (4N) 92:8), the product-containing fractions are concentrated. The residue is dissolved in hot chloroform, the solution is cooled to 0° C. and the crystals are filtered off. After filtration and drying under HV, pure 5-phenyl-7-(3-hydroxyphenyl)-4-aminopyrrolo[2,3-d]pyrimidine having a melting point of 227°–228° C. is obtained. $^1$H—NMR ($d_6$-DMSO): delta (ppm)=6.2 (br. s, 2H), 6.8 (br. d, 1H), 7.2–7.4 (m, 4H), 7.5–7.6 (m, 4H), 7.7 (s, 1H), 8.2 (s, 1H), 9.8 (s, 1H).

EXAMPLE 13

5-(3,4-Methylenedioxyphenyl)-7-(3-ethoxyphenyl)-4-aminopyrrolo-[2,3-d]pyrimidine 0.8 g of 4-(3,4-methylenedioxyphenyl)-1-(3-ethoxyphenyl)-2-amino-3-cyanopyrrole is heated at 160° C. for 6 h in a mixture of 8 ml of formamide, 4 ml of formic acid and 1.5 ml of DMF. After cooling to RT the mixture is treated with water and the crystals obtained are filtered off, washed with water and dried. After chromatography on silica gel (EA/hexane 3:4), the product-containing fractions are concentrated, slurried in ether and filtered. After repeated chromatography on silica gel (methylene chloride/methanol containing $NH_3$ (4N) 97:3), the product-containing fractions are concentrated. The residue is slurried with ether/EA and the crystals are filtered off. 5-(3,4-Methylenedioxyphenyl)-7-(3-ethoxyphenyl)-4-aminopyrrolo-[2,3-d]pyrimidine having a melting point of 153°–155° C. is obtained. $^1$H—NMR ($d_6$-DMSO): delta (ppm)=1.35 (t, 3H), 4.1 (q, 2H), 6.1 (s, 2H), 6.25 (br. s, 2H), 6.9 br. d, 1H), 7.0 (m, 2H), 7.1 (s, 1H), 7.4–7.5 (m, 3H), 7.7 (s, 1H), 8.2 (s, 1H).

(a) 4-(3,4-Methylenedioxyphenyl)-1-(3-ethoxyphenyl)-2-amino-3-cyanopyrrole:

0.19 g of sodium is dissolved in 40 ml of ethanol and subsequently first 0.6 g of malononitrile and then 2.28 g of 2'-(3-ethoxyphenylamino)-3,4-methylenedioxyacetophenone are added at RT and the mixture is stirred at 50° C. for 6 h. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether and the crystals are filtered off, 4-(3,4-methylenedioxyphenyl)-1-(3-ethoxyphenyl)-2-amino-3-cyanopyrrole being obtained. The oily mother liquor also contains mainly 4-(3,4-methylenedioxyphenyl)-1-(3-ethoxyphenyl)-2-amino-3-cyanopyrrole and can also be employed in the next stage.

(b) 2'-(3-Ethoxyphenylamino)-3,4-methylenedioxyacetophenone:

2.4 g of 2'-bromo-3,4-methylenedioxyacetophenone and 1.49 g of m-phenetidine are stirred at 50° C. for 5 h in 30 ml of ethanol in the presence of 2.3 g of powdered $Na_2CO_3$. The mixture is then cooled and concentrated in an RE. The residue is partitioned between water and methylene chloride and the aqueous phase is extracted twice with methylene chloride. The combined organic phases are dried over $Na_2SO_4$ and concentrated. The residue is slurried with ether/petroleum ether and the crystals are filtered off, 2'-(3-ethoxyphenylamino)-3,4-methylenedioxyacetophenone being obtained.

(c) 2'-Bromo-3,4-methylenedioxyacetophenone:

In an analogous manner to that described in Example 3, starting from 3,4-methylenedioxyacetophenone 2'-bromo-3,4-methylenedioxyacetophenone is obtained in crystalline form; this is employed in the next stage without further purification.

EXAMPLE 14

Ethyl 3-(5-phenyl-4-aminopyrrolo[2,3-d]pyrimidin-7-yl)benzoate 0.5 g of ethyl 3-(4-phenyl-2-amino-3-cyanopyrrol-1-yl)benzoate is heated at 190° C. for 6 h in 1 ml of formamide under a nitrogen atmosphere. After cooling to RT the mixture is treated with water and the crystals are filtered off. The mixture is dissolved in a little methylene chloride, dried and concentrated. After chromatography on silica gel (methylene chloride/acetone 5:1), the product-containing fractions are concentrated. Ethyl 3-(5-phenyl-4-aminopyrrolo[2,3-d]pyrimidin-7-yl)benzoate having a melting point of 176°–177° C. is obtained. $^1$H—NMR ($d_6$-DMSO): delta (ppm)=1.4 (t, 3H), 4.4 (q, 2H), 5.2 (br. s, 2H), 7.3 (s, 1H), 7.4–7.65 (m, 6H), ($CDCl_3$) 8.05 (m, 2H), 8.3 (d, 1H), 8.4 (s, 1H).

(a) Ethyl 3-(4-phenyl-2-amino-3-cyanopyrrol-1-yl)benzoate:

0.6 g of piperidine, 0.55 g of malononitrile and a catalytic amount of dimethylaminopyridine are boiled under reflux for 15 h in 50 ml of ethanol together with 2 g of 2'-(3-ethoxycarbonylphenylamino)-acetophenone. The mixture is then cooled and concentrated in an RE. After chromatography on silica gel (methylene chloride), the product-containing fractions are concentrated. The product is dissolved in ether and crystallized by addition of petroleum ether. After filtration, ethyl 3-(4-phenyl-2-amino-3-cyanopyrrol-1-yl)benzoate having a melting point of 129°–130° C. is obtained.

(b) 2'-(3-Ethoxycarbonylphenylamino)acetophenone:

4 g of phenacyl bromide and 5.2 g of ethyl 3-aminobenzoate methanesulfonate are treated with 5.7 ml of triethylamine at RT with stirring in 50 ml of toluene and stirred at RT for 2 h. The mixture is treated with water and washed twice. The organic phase is dried over $MgSO_4$ and the product is crystallized by addition of petroleum ether and by cooling to 0° C. After filtration and drying under HV 2'-(3-ethoxycarbonylphenylamino)acetophenone having a melting point of 116°14 118° C. is obtained.

EXAMPLE 15

3-(5-Phenyl-4-aminopyrrolo[2,3-d]pyrimidin-7-yl)benzoic acid 0.8 g of sodium 3-(4-phenyl-2-amino-3-cyanopyrrol-1-yl)benzoate is heated at 200° C. for 6 h in 1 ml of formamide under a nitrogen atmosphere. After cooling to RT, the mixture is treated with water and acidified with glacial acetic acid. The crystals are filtered off and the product is recrystallized from hot glacial acetic acid. After filtration and drying under HV, pure 3-(5-phenyl-4-amino-pyrrolo[2,3-d]

pyrimidin-7-yl)benzoic acid having a melting point of >300° C. is obtained. $^1$H—NMR (d$_6$-DMSO): delta (ppm)=6.2 (br. s, 2H), 7.4 (m, 1H), 7.45–7.6 (m, 4H), 7.65 (t, 1H), 7.8 (s, 1H), 7.9 (d, 1H), 8.1 (d, 1H), 8.25 (s, 1H), 8.5 (s, 1H).

(a) Sodium 3-(4-phenyl-2-amino-3-cyanopyrrol-1-yl) benzoate:

0.2 g of sodium is dissolved in 30 ml of ethanol and subsequently first 0.55 g of malononitrile and then 2.0 g of 2'-(3-ethoxycarbonylphenylamino)acetophenone (see Ex. 14) are added at RT and the mixture is boiled under reflux for 2 h. The mixture is then cooled and the crystals are filtered off, sodium 3-(4-phenyl-2-amino-3-cyanopyrrol-1-yl)benzoate having a melting point of >300° C. being obtained.

EXAMPLE 16

N-[2-(1-Piperazinyl)ethyl]-3-(5-phenyl-4-aminopyrrolo[2,3-d]pyrimidin-7-yl)-benzamide hydrochloride 1.5 g of 3-(5-phenyl-4-aminopyrrolo[2,3-d]pyrimidin-7-yl)-benzoic acid (Example 15) are dissolved in 40 ml of warm DMF and the solution is cooled to 0° C. The mixture is treated with 0.82 g of carbonyldiimidazole and stirred at 0° C. for 2 h. 0.6 g of 1-(2-aminoethyl)-piperazine is then added dropwise and the mixture is allowed to warm to RT and is stirred for 2 h. The mixture is then concentrated in an RE. The residue is treated with water and methylene chloride and an oil which is insoluble in both phases is filtered off. This oil is dissolved in dilute hydrochloric acid (0.1N), and the aqueous phase is washed with methylene chloride, rendered basic with 1N NaOH and extracted with methylene chloride. The organic phase is dried over MgSO$_4$ and concentrated. The residue is taken up in a little ethanol and adjusted to about pH 3 using ethanolic HCl. The crystals formed are filtered off and dried under HV at 100° C. The hydrochloride of N-[2-(1-piperazinyl)ethyl]-3-(5-phenyl-4-aminopyrrolo[2,3-d]pyrimidin-7-yl)-benzamide having a melting point of about 220° C. is obtained.

EXAMPLE 17

N-(2-Hydroxyethyl)-3-(5-phenyl-4-aminopyrrolo[2,3-d]pyrimidin-7-yl)benzamide 1.0 g of 3-(5-phenyl-4-aminopyrrolo[2,3-d]pyrimidin-7-yl)benzoic acid (Example 15) is dissolved in 25 ml of warm DMF and the solution is cooled to 0° C. The mixture is treated with 0.54 g of carbonyldiimidazole and stirred at RT for 2 h. 0.19 g of ethanolamine is then added dropwise and the mixture is allowed to warm to RT and is stirred for 3 h. The mixture is then concentrated in an RE. The residue is dissolved in methylene chloride and the solution is crystallized overnight at 0° C. After filtration, the residue is dissolved in methylene chloride and chromatographed on silica gel (methylene chloride/methanol 15:1). The product-containing fractions are concentrated and the residue is taken up in a little methylene chloride and crystallized overnight at 0° C. The crystals formed are filtered off and dried under HV. N-(2-Hydroxyethyl)-3-(5-phenyl-4-aminopyrrolo[2,3-d]pyrimidin-7-yl)-benzamide having a melting point of 194°–198° C. is obtained.

In analogy to the above examples, the following compounds are also prepared from the respective substituted or unsubstituted haloacetophenones, in particular bromoacetophenone, and the appropriate unsubstituted or substituted anilines:

EXAMPLE 18

5-Phenyl-7-(3-hydroxymethylphenyl)-4-aminopyrrolo2,3-d]pyrimidine, m.p. 163°–168° C.

EXAMPLE 19

5-Phenyl-7-(3-chlorophenyl)-4-aminopyrrolo[2,3-d]pyrimidine, m.p. 188°–189° C.

REFERENCE EXAMPLE 20

5-(4-Methoxyphenyl)-7-phenyl-4-aminopyrrolo[2,3-d]pyrimidine, m.p. 187°–188° C.

EXAMPLE 21

5-(3,4-Dimethoxyphenyl)-7-phenyl-4-aminopyrrolo[2,3-d]pyrimidine, m.p. 207°–209° C.

EXAMPLE 22

5-Phenyl-7-(3,4-methylenedioxyphenyl)-4-aminopyrrolo[2,3-d]pyrimidine, m.p. 170°–172° C.

EXAMPLE 23

5-Phenyl-7-(3,5-dimethoxyphenyl)-4-aminopyrrolo[2,3-d]pyrimidine, m.p. 147°–149° C.

EXAMPLE 24

5-Phenyl-7-(2-hydroxymethylphenyl)-4-aminopyrrolo[2,3-d]pyrimidine, m.p. 174°–175° C.

EXAMPLE 25

5-(3-Methoxyphenyl)-7-(3-hydroxymethylphenyl)-4-aminopyrrolo[2,3-d]-pyrimidine, m.p. 151°–152° C.

EXAMPLE 26

5-(3-Methoxyphenyl)-7-(3,4-methylenedioxyphenyl)-4-aminopyrrolo[2,3-d]-pyrimidin. m.p. 188°–190° C.

EXAMPLE 27

5-Phenyl-7-[4-(2-hydroxyethyl)-phenyl]-4-aminopyrrolo[2,3-d]-pyrimidine, m.p. 169°–171° C.

EXAMPLE 28

5-(3,4-Dimethoxyphenyl)-7-(3-hydroxymethylphenyl)-4-aminopyrrolo-[2,3-d]pyrimidine, m,p. 225° C.

EXAMPLE 29

5-(4-Benzyloxyphenyl)-7-phenyl-4-aminopyrrolo[2,3-d]pyrimidine, rn.p 180°–181° C.

Starting from the compound of Example 29, 5-(4-benzyloxyphenyl)-7-phenyl-4-aminopyrrolo[2,3-d]pyrimidine, the following compound can be obtained by catalytic hydrogenation analogously to Ex 12:

EXAMPLE 30

5-(4-Hydroxyphenyl)-7-phenyl-4-aminopyrrolo[2,3-d]pyrimidine, m.p. 270°–272° C.

Starting from the compound of Example 1 5,7-diphenyl-4-aminopyrrolo[2,3-d]pyrimidine, the following compounds are obtained in a known manner by halogenation, e.g. using the corresponding N-halosuccinimide:

EXAMPLE 31

5,7-Diphenyl-6-chloro-4-aminopyrrolo[2,3-d]pyrimidine, m.p. 168° C.

EXAMPLE 32

5,7-Diphenyl-6-bromo-4-aminopyrrolo[2,3-d]pyrimidine, m.p. 167°–169° C.

Starting from the compound of Example 18, 5-phenyl-7-(3-hydroxymethylphenyl)-4-aminopyrrolo[2,3-d]pyrimidine, the following compound is obtained in a known manner by treatment with chloroenamine (=1-chloro-N,N,2-trimethylpropenylamine, see, for example, L. Ghosez, Adv. Org. Chem. Vol. 9, Part 1, p. 421):

EXAMPLE 33

5-Phenyl-7-(3-chloromethylphenyl)-4-aminopyrrolo[2,3-d]pyrimidine, m.p. 150° C.

Starting from the compound of Example 33, the following compounds are obtained, for example, by heating with an appropriate amine with or without solvent or by reaction with an amine which has been deprotonated by sodium hydride or another strong base in an inert solvent:

EXAMPLE 34
5-Phenyl-7-[3-(1-imidazolylmethyl)-phenyl]-4-aminopyrrolo[2,3-d]pyrimidine, m.p. 127°–129° C.

EXAMPLE 35
5-Phenyl-7-[3-(2-hydroxyethyl)aminomethylphenyl]-4-aminopyrrolo-[2,3-d]pyrimidine hydrochloride, m.p. 265° C.

Analogously to Example 17, starting from 3-(5-Phenyl-4-aminopyrrolo[2,3-d]pyrimidin-7-yl)-benzoic acid (see Example 15) and the appropriate amine the following compounds are obtained:

EXAMPLE 36
N-(3-Hydroxypropyl)-3-(5-phenyl-4-aminopyrrolo[2,3-d]pyrimidin-7-yl)-benzamide, m.p. 202°–204° C.

EXAMPLE 37
N-(2-(4-Imidazolyl)ethyl)-3-(5-phenyl-4-amino-pyrrolo[2,3-d]pyrimidin-7-yl)-benzamide, m.p. 198°–200° C.

In analogy to the above examples, the following compounds can also be prepared using the operations described or using other, conventional chemical operations:

EXAMPLE 38
5-(4-Hydroxyphenyl)-7-[3-(2-hydroxyethyl)aminomethylphenyl]-4-amino-pyrrolo[2,3-d]pyrimidine, m.p. 165° (decomposition)

EXAMPLE 39
5-(3-Methoxyphenyl)-7-[3-(2-hydroxyethyl)aminomethylphenyl]-4-amino-pyrrolo[2,3-d]pyrimidine or a salt thereof, e.g. the hydrochloride

EXAMPLE 40
5-Phenyl-7-[3-(3-hydroxypropyl)aminomethylphenyl]-4-aminopyrrolo-[2,3-d]pyrimidine or a salt thereof, e.g. the hydrochloride

EXAMPLE 41
5-Phenyl-7-[3-(4-hydroxybutyl)aminomethylphenyl]-4-aminopyrrolo-[2,3-d]pyrimidine or a salt thereof, e.g. the hydrochloride

EXAMPLE 42
5-Phenyl-7-[3-(2-aminoethyl)aminomethylphenyl]-4-aminopyrrolo-[2,3-d]pyrimidine or a salt thereof, e.g. the hydrochloride

EXAMPLE 43
5-Phenyl-7-[3-(3-aminopropyl)aminomethylphenyl]-4-aminopyrrolo[2,3-d]-pyrimidine or a salt thereof, e.g. the hydrochloride

EXAMPLE 44
5-Phenyl-7-[3-(1-piperazinylmethyl)phenyl]-4-aminopyrrolo[2,3-d]pyrimidine or a salt thereof, e.g. the hydrochloride

EXAMPLE 45
5-Phenyl-7-[3-(2-(1-piperazinyl)ethyl)aminomethylphenyl]-4-aminopyrrolo-[2,3-d]pyrimidine or a salt thereof, e.g. the hydrochloride

EXAMPLE 46
5-Phenyl-7-[3-(2-(4-piperidinyl)ethyl)aminomethylphenyl]-4-aminopyrrolo-[2,3-d]pyrimidine or a salt thereof, e.g. the hydrochloride

EXAMPLE 47
5-Phenyl-7-[3-(2-(4-imidazolyl)ethyl)aminomethylphenyl]-4-aminopyrrolo-[2,3-d]pyrimidine or a salt thereof, e.g. the hydrochloride

EXAMPLE 48
5-Phenyl-7-[3-(2-pyridylmethyl)aminomethylphenyl]-4-aminopyrrolo[2,3-d]-pyrimidine or a salt thereof, e.g. the hydrochloride, m.p. of the hydrochloride: 220° C.

EXAMPLE 49
5-Phenyl-7-(4-hydroxymethylphenyl)-4-aminopyrrolo[2,3-d]pyrimidine, m.p. 207°–209° C.

EXAMPLE 50
5-Phenyl-7-(4-chloromethylphenyl)-4-aminopyrrolo[2,3-d]pyrimidine

EXAMPLE 51
5-Phenyl-7-[4-(2-hydroxyethyl)aminomethylphenyl]-4-aminopyrrolo-[2,3-d]pyrimidine, m.p. 120°–122° C., or a salt thereof, e.g. the hydrochloride

EXAMPLE 52
5-Phenyl-7-[4-(3-hydroxypropyl)aminomethylphenyl]-4-aminopyrrolo-[2,3-d]pyrimidine or a salt thereof, e.g. the hydrochloride

EXAMPLE 53
5-Phenyl-7-[4-(2-aminoethyl)aminomethylphenyl]-4-aminopyrrolo[2,3-d]-pyrimidine or a salt thereof, e.g. the hydrochloride

EXAMPLE 54
5-Phenyl-7-[4-(3-aminopropyl)aminomethylphenyl]-4-aminopyrrolo[2,3-d]-pyrimidine or a salt thereof, e.g. the hydrochloride

EXAMPLE 55
5-Phenyl-7-[4-(2-(1-piperazinyl)ethyl)aminomethylphenyl]-4-aminopyrrolo-[2,3-d]pyrimidine or a salt thereof, e.g. the hydrochloride

EXAMPLE 56
5-Phenyl-7-[4-(2-(4-imidazolyl)ethyl)aminomethylphenyl]-4-aminopyrrolo-[2,3-d]pyrimidine or a salt thereof, e.g. the hydrochloride

EXAMPLE 57
5-Phenyl-7-[3-(2-hydroxyethylthiomethyl)phenyl]-4-aminopyrrolo[2,3-d]-pyrimidine

EXAMPLE 58
5-Phenyl-7-[4-(2-hydroxyethylthiomethyl)phenyl]-4-amino-pyrrolo[2,3-d]-pyrimidine

EXAMPLE 59
5-Phenyl-7-[3-(2-hydroxyethylsulfinylmethyl)phenyl]-4-aminopyrrolo[2,3-d]-pyrimidine

EXAMPLE 60
5-Phenyl-7-[4-(2-hydroxyethylsulfinylmethyl)phenyl]-4-amino-pyrrolo[2,3-d]-pyrimidine

EXAMPLE 61
5-Phenyl-7-[3-(2-hydroxyethylsulfonylmethyl)phenyl]-4-aminopyrrolo[2,3-d]-pyrimidine

EXAMPLE 62
5-Phenyl-7-[4-(2-hydroxyethylsulfonylmethyl)phenyl]-4-aminopyrrolo[2,3-d]-pyrimidine

EXAMPLE 63
5-Phenyl-7-(2-chloromethylphenyl)-4-aminopyrrolo[2,3-d]pyrimidine

EXAMPLE 64
5-Phenyl-7-[2-(2-hydroxyethyl)aminomethylphenyl]-4-aminopyrrolo[2,3-d]-pyrimidine, m.p. 170° C., or a salt thereof, e.g. the hydrochloride

EXAMPLE 65
5-Phenyl-7-[2-(3-hydroxypropyl)aminomethylphenyl]-4-amino-pyrrolo[2,3-d]-pyrimidine or a salt thereof, e.g. the hydrochloride

EXAMPLE 66
5-Phenyl-7-[2-(3-aminopropyl)aminomethylphenyl]-4-aminopyrrolo[2,3-d]-pyrimidine or a salt thereof, e.g. the hydrochloride

EXAMPLE 67
5-Phenyl-7-[2-(2-hydroxyethylthiomethyl)phenyl]-4-aminopyrrolo[2,3-d]-pyrimidine

EXAMPLE 68
5-Phenyl-7-[3-cyanophenyl]-4-aminopyrrolo[2,3-d]pyrimidine

EXAMPLE 69
5-Phenyl-7-[3-(1-imidazolyl)phenyl]-4-aminopyrrolo[2,3-d]pyrimidine

EXAMPLE 70
5-Phenyl-7-[4-cyanophenyl]-4-aminopyrrolo[2,3-d]pyrimidine

EXAMPLE 71
5-Phenyl-7-[4-ethoxyphenyl]-4-aminopyrrolo[2,3-d]pyrimidine

EXAMPLE 72
5-Phenyl-7-[4-benzyloxyphenyl]-4-aminopyrrolo[2,3-d]pyrimidine

EXAMPLE 73
5-Phenyl-7-[4-hydroxyphenyl]-4-aminopyrrolo[2,3-d]pyrimidine

EXAMPLE 74
5-Phenyl-7-[2-hydroxyphenyl]-4-aminopyrrolo[2,3-d]pyrimidine

EXAMPLE 75
5-Phenyl-7-[4-(2-hydroxyethoxy)phenyl]-4-aminopyrrolo[2,3-d]pyrimidine

EXAMPLE 76
5-Phenyl-7-[3-(2-hydroxyethoxy)phenyl]-4-aminopyrrolo[2,3-d]pyrimidine, m.p. 119°–126° C.

EXAMPLE 77
5-Phenyl-7-[2-(2-hydroxyethoxy)phenyl]-4-aminopyrrolo[2,3-d]-pyrimidine

EXAMPLE 78
5-(4-Hydroxyphenyl)-7-[4-(2-hydroxyethoxy)phenyl]-4-amino-pyrrolo[2,3-d]-pyrimidine, m.p. 221°–222° C.

EXAMPLE 79
5-(4-Hydroxyphenyl)-7-[3-(2-hydroxyethoxy)phenyl]-4-amino-pyrrolo[2,3-d]-pyrimidine (amorphous foam). The compound is prepared analogously to Examples 1, 29, 30 and 155. The starting material used is 3-(2-hydroxyethoxy) aniline. This is prepared by reaction of 3-fluoronitrobenzene with the monosodium salt of ethylene glycol and subsequent reduction of the nitro group to the amino group.

EXAMPLE 80
5-(3-Methoxyphenyl)-7-[4-(2-hydroxyethoxy)phenyl]-4-aminopyrrolo[2,3-d]-pyrimidine

EXAMPLE 81
5-(3-Methoxyphenyl)-7-[3-(2-hydroxyethoxy)phenyl]-4-aminopyrrolo[2, 3-d]-pyrimidine, m.p. 163°–165° C.

EXAMPLE 82
5-(4-Methoxyphenyl)-7-[3-(2-hydroxyethoxy)phenyl]-4-aminopyrrolo[2,3-d]-pyrimidine

EXAMPLE 83
5-(4-Fluorophenyl)-7-[3-(2-hydroxyethoxy)phenyl]-4-aminopyrrolo[2,3-d]-pyrimidine

EXAMPLE 84
5-(3-Chlorophenyl)-7-[3-(2-hydroxyethoxy)phenyl]-4-aminopyrrolo[2,3-d]-pyrimidine

EXAMPLE 85
5-Phenyl-7-[3-(3-hydroxypropoxy)phenyl]-4-aminopyrrolo[2,3-d]pyrimidine

EXAMPLE 86
5-(4-Hydroxyphenyl)-7-[3-(3-hydroxypropoxy)phenyl]-4-amino-pyrrolo[2,3-d]-pyrimidine

EXAMPLE 87
5-(3-Methoxyphenyl)-7-[3-(3-hydroxypropoxy)phenyl]-4-aminopyrrolo[2,3-d]-pyrimidine

EXAMPLE 88
5-Phenyl-7-[4-(3-hydroxypropoxy)phenyl]-4-aminopyrrolo[2,3-d]pyrimidine

EXAMPLE 89
5-(4-Hydroxyphenyl)-7-[4-(3-hydroxypropoxy)phenyl]-4-aminopyrrolo[2,3-d]-pyrimidine

EXAMPLE 90
5-(3-Methoxyphenyl)-7-[4-(3-hydroxypropoxy)phenyl]-4-aminopyrrolo[2,3-d]-pyrimidine

EXAMPLE 91
5-Phenyl-7-[2-(3-hydroxypropoxy)phenyl]-4-aminopyrrolo[2,3-d]pyrimidine

EXAMPLE 92
5-Phenyl-7-[4-(2-aminoethoxy)phenyl]-4-aminopyrrolo[2,3d]pyrimidine

EXAMPLE 93
5-Phenyl-7-[3-(2-aminoethoxy)phenyl]-4-aminopyrrolo[2,3d]pyrimidine

EXAMPLE 94
5-Phenyl-7-[2-(2-aminoethoxy)phenyl]-4-aminopyrrolo[2,3d]pyrimidine

EXAMPLE 95
5-(4-Hydroxyphenyl)-7-[4-(2-aminoethoxy)phenyl]-4-aminopyrrolo[2,3-d]-pyrimidine

EXAMPLE 96
5-(4-Hydroxyphenyl)-7-[3-(2-aminoethoxy)phenyl]-4-aminopyrrolo[2,3-d]-pyrimidine

EXAMPLE 97
5-(3-Methoxyphenyl)-7-[4-(2-aminoethoxy)phenyl]-4-aminopyrrolo[2,3-d]-pyrimidine

EXAMPLE 98
5-(3-Methoxyphenyl)-7-[3-(2-aminoethoxy)phenyl]-4-aminopyrrolo[2,3-d]-pyrimidine

EXAMPLE 99
5-(4-Methoxyphenyl)-7-[3-(2-aminoethoxy)phenyl]-4-aminopyrrolo[2,3-d]-pyrimidine

EXAMPLE 100
5-Phenyl-7-[3-(3-aminopropoxy)phenyl]-4-aminopyrrolo[2,3-d]pyrimidine

EXAMPLE 101
5-(4-Hydroxyphenyl)-7-[3-(3-aminopropoxy)phenyl]-4-aminopyrrolo[2,3-d]-pyrimidine

EXAMPLE 102
5-(3-Methoxyphenyl)-7-[3-(3-aminopropoxy)phenyl]-4-aminopyrrolo[2,3-d]-pyrimidine

EXAMPLE 103
5-Phenyl-7-[4-(3-aminopropoxy)phenyl]-4-aminopyrrolo[2,3-d]pyrimidine

EXAMPLE 104
5-(4-Hydroxyphenyl)-7-[4-(3-aminopropoxy)phenyl]-4-aminopyrrolo[2,3-d]-pyrimidine

EXAMPLE 105
5-(3-Methoxyphenyl)-7-[4-(3-aminopropoxy)phenyl]-4-aminopyrrolo[2,3-d]-pyrimidine

EXAMPLE 106
5-Phenyl-7-[2-(3-aminopropoxy)phenyl]-4-aminopyrrolo[2,3-d]pyrimidine

EXAMPLE 107
5-Phenyl-7-[3-(2-(1-piperazinyl)ethoxy)phenyl]-4-aminopyrrolo[2,3-d]-pyrimidine or a salt thereof, e.g. the hydrochloride

EXAMPLE 108
5-Phenyl-7-[3-(2-(1-imidazolyl)ethoxy)phenyl]-4-aminopyrrolo[2,3-d]-pyrimidine, m.p. 166°–168° C., or a salt thereof, e.g. the hydrochloride. The free compound is prepared from 5-phenyl-7-[3-(2-chloroethoxy)phenyl]-4-aminopyrrolo[2,3-d]pyrimidine and imidazolyl analogously to Example 155. 5-Phenyl-7-[3-(2-chloroethoxy)phenyl]-4-aminopyrrolo[2,3-d]pyrimidine is obtained according to the usual synthetic sequence starting from phenacyl bromide and 3-(2-chloroethoxy)aniline [see Example 155 a)].

EXAMPLE 109
5-Phenyl-7-[3-(2-(2-hydroxyethylamino)ethoxy)phenyl]-4-aminopyrrolo[2,3-d]-pyrimidine, m.p. 188°–189° C., or a salt thereof, e.g. the hydrochloride. The free compound is obtained by reaction of 5-phenyl-7-[3-(2-chloroethoxy)phenyl]-4-aminopyrrolo[2,3-d]-pyrimidine (see Example 108) and 2-aminoethanol.

EXAMPLE 110
5-Phenyl-7-[3-(2-(2-aminoethylamino)ethoxy)phenyl]-4-aminopyrrolo[2,3-d]-pyrimidine or a salt thereof, e.g. the hydrochloride

EXAMPLE 111
5-Phenyl-7-[3-(2-(2-(4-imidazolyl)ethylamino)ethoxy)phenyl]-4-aminopyrrolo-[2,3-d]pyrimidine or a salt thereof, e.g. the hydrochloride

EXAMPLE 112
5-Phenyl-7-[4-(2-(1-piperazinyl)ethoxy)phenyl]-4-aminopyrrolo[2,3-d]-pyrimidine or a salt thereof, e.g. the hydrochloride

EXAMPLE 113
5-Phenyl-7-[4-(2-(1-imidazolyl)ethoxy)phenyl]-4-aminopyrrolo[2,3-d]pyrimidine or a salt thereof, e.g. the hydrochloride

EXAMPLE 114
5-Phenyl-7-[4-(2-(2-hydroxyethylamino)ethoxy)phenyl]-4-aminopyrrolo[2,3-d]-pyrimidine or a salt thereof, e.g. the hydrochloride

EXAMPLE 115
5-Phenyl-7-[4-(2-hydroxyethylthio)phenyl]-4-aminopyrrolo[2,3-d]pyrimidine

EXAMPLE 116
5-Phenyl-7-[3-(2-hydroxyethylthio)phenyl]-4-aminopyrrolo[2,3-d]pyrimidine, m.p. 147°–150° C.

EXAMPLE 117
5-Phenyl-7-[4-(3-hydroxypropylthio)phenyl]-4-aminopyrrolo[2,3-d]pyrimidine

EXAMPLE 118
5-Phenyl-7-[3-(3-hydroxypropylthio)phenyl]-4-aminopyrrolo[2,3-d]pyrimidine

EXAMPLE 119
5-Phenyl-7-[4-(2-aminoethylthio)phenyl]-4-aminopyrrolo[2,3-d]pyrimidine

EXAMPLE 120
5-Phenyl-7-[3-(2-aminoethylthio)phenyl]-4-aminopyrrolo[2,3-d]pyrimidine

EXAMPLE 121
5-Phenyl-7-[4-(3-aminopropylthio)phenyl]-4-aminopyrrolo[2,3-d]pyrimidine

EXAMPLE 122
5-Phenyl-7-[3-(3-aminopropylthio)phenyl]-4-aminopyrrolo[2,3-d]pyrimidine

EXAMPLE 123
5-Phenyl-7-[4-(2-hydroxyethylsulfinyl)phenyl]-4-aminopyrrolo[2,3-d]pyrimidine

EXAMPLE 124
5-Phenyl-7-[3-(2-hydroxyethylsulfinyl)phenyl]-4-aminopyrrolo[2,3-d]-pyrimidine, m.p. 177°–180° C.

EXAMPLE 125
5-Phenyl-7-[4-(3-hydroxypropylsulfinyl)phenyl]-4-aminopyrrolo[2,3-d]-pyrimidine

EXAMPLE 126
5-Phenyl-7-[3-(3-hydroxypropylsulfinyl)phenyl]-4-aminopyrrolo[2,3-d]-pyrimidine

EXAMPLE 127
5-Phenyl-7-[4-(2-aminoethylsulfinyl)phenyl]-4-aminopyrrolo[2,3-d]pyrimidine

EXAMPLE 128
5-Phenyl-7-[3-(2-aminoethylsulfinyl)phenyl]-4-aminopyrrolo[2,3-d]pyrimidine

EXAMPLE 129
5-Phenyl-7-[4-(3-aminopropylsulfinyl)phenyl]-4-aminopyrrolo[2,3-d]pyrimidine

EXAMPLE 130
5-Phenyl-7-[3-(3-aminopropylsulfinyl)phenyl]-4-aminopyrrolo[2,3-d]pyrimidine

EXAMPLE 131
5-Phenyl-7-[4-(2-hydroxyethylsulfonyl)phenyl]-4-aminopyrrolo[2,3-d]-pyrimidine

EXAMPLE 132
5-Phenyl-7-[3-(2-hydroxyethylsulfonyl)phenyl]-4-aminopyrrolo[2,3-d]-pyrimidine, m.p. 193°–195° C.

EXAMPLE 133
5-Phenyl-7-[4-(3-hydroxypropylsulfonyl)phenyl]-4-aminopyrrolo[2,3-d]-pyrimidine

EXAMPLE 134
5-Phenyl-7-[3-(3-hydroxypropylsulfonyl)phenyl]-4-aminopyrrolo[2,3-d]-pyrimidine

EXAMPLE 135
5-Phenyl-7-[4-(2-aminoethylsulfonyl)phenyl]-4-aminopyrrolo[2,3-d]pyrimidine

EXAMPLE 136
5-Phenyl-7-[3-(2-aminoethylsulfonyl)phenyl]-4-aminopyrrolo[2,3-d]pyrimidine

EXAMPLE 137
5-Phenyl-7-[4-(3-aminopropylsulfonyl)phenyl]-4-aminopyrrolo[2,3-d]pyrimidine

EXAMPLE 138
5-Phenyl-7-[3-(3-aminopropylsulfonyl)phenyl]-4-aminopyrrolo[2,3-d]pyrimidine

EXAMPLE 139
N-(2-(Hydroxysulfonylethyl)-3-(5-phenyl-4-aminopyrrolo[2,3-d]pyrimidin-7-yl)-benzamide

EXAMPLE 140
5-Phenyl-7-[3-(2-hydroxysulfonylethoxy)phenyl]-4-aminopyrrolo[2,3-d]-pyrimidine

EXAMPLE 141
5-(4-Hydroxyphenyl)-7-(3-hydroxyphenyl)-4-aminopyrrolo[2,3-d]pyrimidine, m.p. 250°–252° C.

EXAMPLE 142
5-(4-Hydroxyphenyl)-7-(3,4-methylenedioxyphenyl)-4-aminopyrrolo[2,3-d]-pyrimidine, m.p. 258°–260° C.

EXAMPLE 143
5-(4-Hydroxyphenyl)-7-(3-hydroxymethylphenyl)-4-aminopyrrolo[2,3-d]-pyrimidine, m.p. 234°–236° C.

EXAMPLE 144
5-(4-Hydroxyphenyl)-7-(3-chlorophenyl)-4-aminopyrrolo[2,3-d]pyrimidine, m.p. 240°–242° C.

EXAMPLE 145
5-(4-Hydroxyphenyl)-7-[3-(3-hydroxypropylaminomethyl)phenyl]-4-aminopyrrolo[2,3-d]pyrimidine or a salt thereof, e.g. the hydrochloride, amorphous foam

EXAMPLE 146
5-(4-Hydroxyphenyl)-7-[4-(2-hydroxyethyl)phenyl]-4-aminopyrrolo[2,3-d]-pyrimidine, m.p. 222°–226° C.

EXAMPLE 147
5-(4-Hydroxyphenyl)-7-[4-(2-formyloxyethyl)phenyl]-4-aminopyrrolo[2,3-d]-pyrimidine, m.p. 209°–211° C.

EXAMPLE 148
5-Phenyl-7-[3-(2-formyloxyethoxy)phenyl]-4-aminopyrrolo[2,3-d]pyrimidine, m.p. 136°–138° C.

EXAMPLE 149
5-Phenyl-7-[3-(2-(N-morpholino)ethoxy)phenyl]-4-aminopyrrolo[2,3-d]-pyrimidine, m.p. 92°–97° C. The compound is obtained by reaction of 5-phenyl-7-[3-(2-chloroethoxy)phenyl]-4-aminopyrrolo[2,3-d]pyrimidine (see Example 108) and morpholine.

EXAMPLE 150
5-Phenyl-7-[3-(2-N,N-dimethylaminoethoxy)phenyl]-4-aminopyrrolo[2,3-d]-pyrimidine, m.p. 127°–129° C. The compound is obtained by reaction of 5-phenyl-7-[3-(2-chloroethoxy)phenyl]-4-aminopyrrolo[2,3-d]pyrimidine (see Example 108) and dimethylamine.

EXAMPLE 151
5-(3-Hydroxyphenyl)-7-phenyl-4-aminopyrrolo[2,3-d]pyrimidine, m.p. 245°–247° C.

EXAMPLE 152
5-(4-Hydroxy-3-methylphenyl)-7-phenyl-4-aminopyrrolo[2,3-d]pyrimidine, m.p. 215°–218° C.

EXAMPLE 153
5-(4-Hydroxy-3-methoxyphenyl)-7-phenyl-4-aminopyrrolo[2,3-d]pyrimidine, m.p. 212°–214° C.

EXAMPLE 154
5-(4-Hydroxymethylphenyl)-7-phenyl-4-aminopyrrolo[2,3-d]pyrimidine, m.p. 178°–180° C.

EXAMPLE 155
5-(4-Hydroxyphenyl)-7-[3-(2-(1-imidazolyl)ethoxy)phenyl]-4-aminopyrrolo-[2,3-d]pyrimidine.

0.96 g of 5-(4-benzyloxyphenyl)-7-[3-(2-chloroethoxy)phenyl]-4-aminopyrrolo[2,3-d]-pyrimidine and 0.22 g of imidazolyl sodium are heated to 60° C. in 25 ml of DMF and the mixture is stirred for 14 h. The mixture is then cooled to RT and concentrated in an RE. The residue is treated with water, extracted 3 times with ethyl acetate and concentrated. The residue is crystallized from ethanol/methylene chloride and the crystals are filtered off and washed with ethanol. After drying under HV, 5-(4-benzyloxyphenyl)-7-[3-(2-(1-imidazolyl)-ethoxy)phenyl]-4-aminopyrrolo[2,3-d]pyrimidine having an m.p. of 183°–186° C. is obtained.

0.9 g of 5-(4-benzyloxyphenyl)-7-[3-(2-(1-imidazolyl)ethoxy)phenyl]-4-aminopyrrolo[2,3-d]-pyrimidine is hydrogenated for 35 h in a hydrogen atmosphere at normal pressure and about 40° C. in 40 ml of THF and 10 ml of ethanol in the presence of 0.15 g of 10% palladium/carbon. After filtration through Hyflo, the mixture is concentrated. The residue is chromatographed on silica gel (methylene chloride/methanol 9:1), and the product-containing fractions are combined and concentrated. The residue is slurried in ether and the crystals are filtered off and washed with ether. After drying under HV, 5-(4-hydroxyphenyl)-7-[3-(2-(1-imidazolyl)ethoxy)phenyl]4-aminopyrrolo[2,3-d]pyrimidine having an m.p. of 217°–220° C. is obtained.

The starting compound is prepared as follows:
a) 3-(2-Chloroethoxy)aniline:

60 g of 3-nitrophenol, 88 g of potassium carbonate and 178 ml of 1-bromo-2-chloroethane are boiled under reflux for 36 h in 800 ml of acetone together with 1.5 g of tetrabutylammonium bromide and 2.0 g of potassium iodide. The mixture is then cooled to RT and concentrated in an RE. The mixture is treated with water, extracted 3 times with ethyl acetate and concentrated. The residue is chromatographed using methylene chloride and the product-containing fractions are concentrated. 1-(2-chloroethoxy)-3-nitrobenzene are obtained as an oil which may crystallize (m.p. 58°–60° C).

85.5 g of 1-(2-chloroethoxy)-3-nitrobenzene are hydrogenated at normal pressure in a hydrogen atmosphere at RT for 4 h in 800 ml of ethanol. After filtration through Celite and concentration in an RE, 3-(2-chloroethoxy)aniline is obtained as an oil (Rf=0.4 silica gel, hexane/EA 2:1).

(b) 2'-(3-(2-Chloroethoxy)phenylamino)-4-benzyloxyacetophenone:

16.1 g of 4-benzyloxy-phenacyl bromide and 9.5 g of 3-(2-chloroethoxy)aniline are stirred at 50° C. for 1.5 h in 150 ml of ethanol in the presence of 6.7 g of powdered $Na_2CO_3$. The mixture is then cooled and concentrated in an RE. The residue is partitioned between water and EA and the insoluble solid is filtered off, a first batch of 2'-(3-(2-chloroethoxy)phenylamino)-4-benzyloxy-acetophenone (m.p. 159°–160° C.) being obtained. The two-phase mother liquor is extracted and the aqueous phase is re-extracted twice with EA. The combined organic phases are dried over $Na_2SO_4$ and concentrated. The residue is slurried with ether and the crystals are filtered off, the second batch of 2'-(3-(2-chloroethoxy)phenylamino)-4-benzyloxyacetophenone being obtained. Further 2'-(3-(2-chloroethoxy)phenylamino)-4-benzyloxyacetophenone (m.p. 157°–159° C.) is again obtained from the mother liquor by addition of petroleum ether.

(c) 4-(4-Benzyloxyphenyl)-1-[3-(2-chloroethoxy)phenyl]-2-amino-3-cyanopyrrole:

1.32 g of sodium are dissolved in 250 ml of ethanol and subsequently first 4.12 g of malononitrile and then 20.6 g of 2'-(3-(2-chloroethoxy)phenylamino)-4-benzyloxyacetophenone suspended in 700 ml of THF are added at RT and the mixture is stirred at 50° C. for 15 h. After addition of a further 0.13 g of sodium and 0.4 g of malononitrile the mixture is again stirred at 50° C. for 24 h. The mixture is then cooled and concentrated in an RE. The residue is slurried in EA/ether and the solid is filtered off and washed with EA/ether. 4-(4-Benzyloxyphenyl)-1-[3-(2-chloroethoxy)phenyl]-2-amino-3-cyanopyrrole of m.p. 77°–79° C. is obtained. The mother liquor is concentrated, the residue is dissolved in methylene chloride and the solution is filtered through a little silica gel. The mother liquor is concentrated, taken up in ether and a second batch of 4-(4-benzyloxyphenyl)-1-[3-(2-chloroethoxy)phenyl]-2-amino-3-cyanopyrrole of m.p. 84°–87° C. crystallizes at 0° C.

(d) 4-(4-Benzyloxyphenyl)-1-[3-(2-chloropethoxy)phenyl]-2-(N-ethoxyformimidato)-3-cyanopyrrole:

15.2 g of 4-(4-benzyloxyphenyl)-1-[3-(2-chloroethoxy) phenyl]-2-amino-3-cyanopyrrole and 0.5 ml of acetic anhydride are heated at 90° C. for 6.5 h in 200 ml of triethyl orthoformate. After cooling to RT, the mixture is concentrated in an RE. The residue is slurried in ether and the solid is filtered off and washed with ether. 4-(4-Benzyloxyphenyl)-1-[3-(2-chloroethoxy)phenyl]-2-(N-ethoxyformimidato)-3-cyanopyrrole of m.p. 169°–171° C. is obtained.

(e) 4-(4-Benzyloxyphenyl)-1-[3-(2-chloroethoxy)phenyl]-2-(N-formamidino)-3-cyanopyrrole:

350 ml of ammonia in methanol (about 8%) and 13.5 g of 4-(4-benzyloxyphenyl)-1-[3-(2-chloroethoxy)phenyl]-2-(N-ethoxyformimidato)-3-cyanopyrrole are stirred at RT for 12 h. 200 ml of methylene chloride and 100 ml of methanol in ammonia (about 8%) are then added and the solution is stirred at RT for a further 60 h. The mixture is then concentrated and the residue is slurried with methanol/ether, cooled to 0° C. and the crystals are filtered off. After filtration and drying under HV, 4-(4-benzyloxyphenyl)-1-[3-(2-chloroethoxy)phenyl]-2-(N-formamidino)-3-cyanopyrrole having a melting point of 151°–154° C. is obtained.

(f) 5-(4-Benzyloxyphenyl)-7-[3-(2-chloroethoxy)phenyl]-4-aminopyrrolo[2,3-d]pyrimidine:

0.1 g of sodium is dissolved in 200 ml of ethanol and 10.5 g of 4-(4-benzyloxyphenyl)-1-[3-(2-chloroethoxy)phenyl]-2-(N-formamidino)-3-cyanopyrrole are then added and the mixture is heated to 50° C. and stirred for 1 h. The mixture is then cooled and concentrated in an RE. The residue is treated with water, extracted 3 times with EA and concentrated. The residue is slurried in ether/EA, cooled to 0° C. and the solid is filtered off and washed with ether. 5-(4-Benzyloxyphenyl)-7-[3-(2-chloroethoxy)phenyl]-4-aminopyrrolo[2,3-d]pyrimidine having a melting point of 146°–148° C. is obtained.

EXAMPLE 156

5-(4-Hydroxyphenyl)-7-[4-(2-(1-imidazolyl)ethoxy)phenyl]-4-aminopyrrolo-[2,3-d]pyrimidine Starting from the 4-(2-chloroethoxy)aniline prepared from 4-nitrophenol and chlorobromomethane with subsequent catalytic hydrogenation analogously to Example 155 using known methods and from the 4-benzyloxyphenacyl bromide prepared from 4-hydroxyacetophenone by benzylation and bromination with bromine or copper bromide using known methods, 5-(4-benzyloxyphenyl)-7-[4-(2-chloroethoxy)phenyl]-4-aminopyrrolo-[2,3-d]pyrimidine, m.p. 188°–190° C., is obtained in an analogous sequence to Example 155.

0.8 g of 5-(4-benzyloxyphenyl)-7-[4-(2-chloroethoxy) phenyl]-4-aminopyrrolo[2,3-d]pyrimidine and 0.2 g of sodium imidazole are heated to 70° C. in 30 ml of DMF and the mixture is stirred for 3 h. The mixture is then cooled to RT and treated with water, extracted 3 times with methylene chloride and concentrated. After chromatography on silica gel (methylene chloride/methanol 15:1) and crystallization from ether/methylene chloride, 5-(4-benzyloxy-phenyl)-7-[4-(2-(1-imidazolyl)ethoxy)phenyl]-4-aminopyrrolo[2,3-d] pyrimidine having an m.p. of 105°–107° C. is obtained.

0.5 g of 5-(4-benzyloxyphenyl)-7-[4-(2-(1-imidazolyl) ethoxy)phenyl]-4-aminopyrrolo[2,3-d]-pyrimidine is hydrogenated for 22 h in a hydrogen atmosphere at normal pressure and about 50° C. in 15 ml of THF in the presence of 0.1 g of 5% palladium/carbon. After filtration through Celite and crystallization by addition of ether, 5-(4-hydroxyphenyl)-7-[4-(2-(1-imidazolyl)ethoxy)phenyl]-4-aminopyrrolo[2,3-d]pyrimidine having an m.p. of 210°–212° C. is obtained.

EXAMPLE 157

5-(3-Hydroxyphenyl)-7-[3-(2-(1-imidazolyl)ethoxy)phenyl]-4-aminopyrrolo-[2,3-d]pyrimidine Starting from the 3-(2-chloroethoxy)aniline prepared in Example 155 from 3-nitrophenol and chlorobromomethane with subsequent catalytic hydrogenation and from the 3-benzyloxy-phenacyl bromide prepared using known methods from 3-hydroxyacetophenone by benzylation and bromination with bromine or copper bromide, 5-(3-benzyloxyphenyl)-7-[3-(2-chloroethoxy)phenyl]-4-aminopyrrolo[2,3-d]pyrimidine, Rf=0.1 (Hex/EA 1:1, silica gel) is prepared in an analogous sequence.

2 g of 5-(3-benzyloxyphenyl)-7-[3-(2-chloroethoxy) phenyl]-4-aminopyrrolo[2,3-d]pyrimidine (Ex. 153) and 0.46 g of imidazolyl sodium are heated to 50° C. in 45 ml of DMF and the mixture is stirred for 15 h. The mixture is then cooled to RT and treated with water, extracted 3 times with ethyl acetate and concentrated. After chromatography on silica gel (methylene chloride/methanol containing 5% of about 5N ammonia in methanol), 5-(3-benzyloxyphenyl)-7-[3-(2-(1-imidazolyl)ethoxy)phenyl]-4-aminopyrrolo[2,3-d] pyrimidine having an Rf=0.4 (silica gel, methylene chloride/methanol containing 5% of about 5N ammonia in methanol= 9:1) is obtained.

1.85 g of 5-(3-benzyloxyphenyl)-7-[3-(2-(1-imidazolyl) ethoxy)phenyl]-4-aminopyrrolo[2,3-d]-pyrimidine are hydrogenated in a hydrogen atmosphere at normal pressure and about 40° C. for 80 h in 40 ml of THF in the presence of 0.4 g of 5% palladium/carbon. After filtration through Celite and crystallization from ethanol, 5-(3-hydroxyphenyl)-7-[3-(2-(1-imidazolyl)-ethoxy)phenyl]-4-aminopyrrolo[2,3-d]pyrimidine having a melting point of 165°–167° C. is obtained.

EXAMPLE 158
5-(3-Hydroxyphenyl)-7-[4-(2-N,N-dimethylaminoethoxy) phenyl]-4-amino-pyrrolo[2,3-d]pyrimidine, and

EXAMPLE 159
5-(3-Hydroxyphenyl)-7-[4-(2-(2-hydroxyethylamino) ethoxy)phenyl]-4-amino-pyrrolo[2,3-d]pyrimidine Starting from the 4-(2-chloro-1-ethoxy)aniline prepared in analogy to Example 155 from 4-nitrophenol and chlorobromomethane with subsequent catalytic hydrogenation and from the 3-benzyloxyphenacyl bromide prepared from 3-hydroxyacetophenone by benzylation and bromination with bromine or copper bromide using known methods, 5-(3-benzyloxy-phenyl)-7-[4-(2-chloro-1-ethoxy)phenyl]-4-aminopyrrolo[2,3-d]pyrimidine (Rf=0.27, silica gel, hexane/EA 1:2) is obtained in an analogous sequence.

Analogously to Example 157, 2 g of 5-(3-benzyloxyphenyl)-7-[4-(2-chloroethoxy)phenyl]-4-aminopyrrolo[2,3-d]pyriimidine (preparation see Example 157) and 0.38 ml of ethanolamine in 20 ml of DMF are heated at 50° C. for 15 h with stirring and, after addition of 0.8 ml of ethanolamine, again heated at 70° C. for 15 h. The mixture is then cooled to RT and treated with water, extracted 3 times with EA and concentrated. After chromatography on silica gel (methylene chloride/methanol containing 5% of about 5N ammonia in methanol 9:1), first 5-(3-benzyloxyphenyl)-7-[4-(2-N,N-dimethylaminoethoxy) phenyl]-4-aminopyrrolo[2,3-d]pyrimidine (Rf=0.3) and then 5-(3-benzyloxyphenyl)-7-[4-(2-(2-hydroxyethylamino) ethoxy)phenyl]-4-aminopyrrolo[2,3-d]rimidine (Rf=0.12) are eluted.

Catalytic hydrogenation of 5-(3-benzyloxyphenyl)-7-[4-(2-N,N-dimethylaminoethoxy)phenyl]-4-aminopyrrolo[2,3-d]pyrimidine analogously to Example 151 in THF in the presence of Pd/C 5% affords, after working up, 5-(3-hydroxyphenyl)-7-[4-(2-N,N-dimethylaminoethoxy)-phenyl]-4-amino-pyrrolo[2,3-d]pypyrimidine having an m.p. of 224°–226° C.

Catalytic hydrogenation of 5-(3-benzyloxyphenyl)-7-[4-(2(2-hydroxyethylamino)ethoxy)-phenyl]-4-aminopyrrolo [2,3-d]pyrimidine analogously to Example 151 in THF in the presence of Pd/C 5% affords, after working up, 5-(3-hydroxyphenyl)-7-[4-(2-(2-hydroxyethylamino)ethoxy) phenyl]-4-amino-pyrrolo[2,3-d]pyrimidine having an m.p. of 200°–202° C.

5-(3-Hydroxyphenyl)-7-[4-(2-(2-hydroxyethylamino) ethoxy)phenyl]-4-aminopyrrolo[2,3-d]-pyrimidine (Example 159) can also be prepared, for example, from 5-(3-benzyloxyphenyl)- 7-[4-(2-chloroethoxy)phenyl]-4-aminopyrrolo[2,3-d]pyrimidine by heating in an excess of ethanolamine without solvent and subsequent catalytic hydrogenation.

EXAMPLE 160
5-(3-Hydroxyphenyl)-7-[3-(3-(1-imidazolyl)propoxy) phenyl)-4-aminopyrrolo-[2,3-d]pyrimidine Starting from the 3-(3-chloro-1-propoxy)aniline prepared from 3-nitrophenol and 1-bromo-3-chloropropane with subsequent catalytic hydrogenation in analogy to Example 155 and from the 3-benzyloxyphenacyl bromide prepared from 3-hydroxyacetophenone by benzylation and bromination with bromine or copper bromide using known methods, 5-(3-benzyloxyphenyl)-7-[3-(3-chloro-1-propoxy)phenyl]-4-aminopyrrolo[2,3-d]pyrimidine (Rf=0.2, silica gel, hexane/EA 1:1) is obtained in an analogous sequence.

1.5 g of 5-(3-benzyloxyphenyl)-7-[3-(3-chloro-1-propoxy)phenyl]-4-aminopyrrolo[2,3-d]-pyrimidine and 0.33 g of imidazolyl sodium are heated to 50° C. in 30 ml of DMF and the mixture is stirred overnight. It is then cooled to RT, the solvent is stripped off in an RE and the mixture is treated with water, extracted 3 times with ethyl acetate and concentrated. 5-(3-benzyloxyphenyl)-7-[3-(3-(1-imidazolyl)propoxy)phenyl]-4-aminopyrrolo[2,3-d]-pyrimidine, (Rf=0.44, silica gel, methylene chloride/methanol containing 5% of about 5N ammonia in methanol 9:1) is obtained.

1.35 g of 5-(3-benzyloxyphenyl)-7-[3-(3-(1-imidazolyl) propoxy)phenyl]-4-aminopyrrolo[2,3-d]-pyrimidine are hydrogenated in a hydrogen atmosphere at normal pressure and about 40° C. for 16 h in 30 ml of methanol in the presence of 0.3 g of 5% palladium/carbon. After filtration through Celite, the solvent is stripped off and the residue is slurried in ether, filtered, slurried again in EA, filtered and dried. 5-(3-Hydroxyphenyl)-7-[3-(3-(1-imidazolyl) propoxy)phenyl]-4-aminopyrrolo[2,3-d]pyrimidine having an m.p. of 120°–122° C. is obtained.

Analogously to Examples 158 and 159, starting from 5-(3-benzyloxyphenyl)-7-[3-(3-chloro-1-propoxy)phenyl]-4-aminopyrrolo[2,3-d]pyrimidine (see Example 160) the following compounds are obtained in two steps:

EXAMPLE 161
5-(3-Hydroxyphenyl)-7-[3-(3-N,N-dimethylaminopropoxy) phenyl]-4-amino-pyrrolo[2,3-d]pyrimidine, m.p. 169°–172° C.

EXAMPLE 162
5-(3-Hydroxyphenyl)-7-[3-(3-(2-hydroxyethylamino) propoxy)phenyl]-4-amino-pyrrolo[2,3-d]pyrimidine, m.p. 124°–126° C.

5-(3-Hydroxyphenyl)-7-[3-(3-(2-hydroxyethylamino) propoxy)phenyl]-4-aminopyrrolo[2,3-d]-pyrimidine (Example 162) can also be prepared, for example, from 5-(3-benzyloxyphenyl)-7-[3-(3-chloro-1-propoxy)phenyl]-4-aminopyrrolo[2,3-d]pyrimidine by heating in an excess of ethanolamine without solvent and subsequent catalytic hydrogenation.

EXAMPLE 163
5-(3-Hydroxyphenyl)-7-[4-(2-(1-imidazolyl)ethoxy)phenyl] -4-aminopyrrolo-[2,3-d]pyrimidine 2.0 g of 5-(3-benzyloxyphenyl)-7-[4-(2-chloro-1-ethoxy) phenyl]-4-aminopyrrolo[2,3-d]-pyrimidine (see Examples 158/159) and 0.46 g of sodium imidazole are heated to 50° C. in 40 ml of DMF and the mixture is stirred for 15 h. The mixture is then cooled to RT and treated with water, extracted 3 times with ethyl acetate and concentrated. The solvent is stripped off in an RE and the mixture is treated with water, extracted 3 times with EA and concentrated. The residue is suspended in ether and, after filtration and drying under HV, 5-(3-benzyloxyphenyl)-7-[4-(2-(1-imidazolyl) ethoxy)phenyl]-4-aminopyrrolo[2,3-d]pyrimidine, (Rf= 0.13, silica gel, methylene chloride/methanol containing 5% of about 5N ammonia in methanol 9:1) is obtained.

1.7 g of 5-(3-benzyloxyphenyl)-7-[4-(2-(1-imidazolyl) ethoxy)phenyl]-4-aminopyrrolo[2,3-d]-pyrimidine are hydrogenated in a hydrogen atmosphere at normal pressure and about 40° C. for 24 h in 40 ml of methanol in the presence of 0.4 g of 5% palladium/carbon. After filtration through Celite and chromatography on silica gel (methylene chloride/methanol containing 5% of about 5N ammonia in methanol 9:1), 5-(3-hydroxyphenyl)-7-[4-(2-(1-imidazolyl) ethoxy)phenyl]-4-aminopyrrolo[2,3-d]pyrimidine having an m.p. of 221°–223° C. is obtained.

EXAMPLE 164

5-(4-Hydroxyphenyl)-7-[3-(3-(1-imidazolyl)propoxy) phenyl]-4-aminopyrrolo-[2,3-d]pyrimidine Starting from the 3-(3-chloro-1-propoxy)aniline prepared from 3-nitrophenol and 1-bromo-3-chloropropane with subsequent catalytic hydrogenation in analogy to Example 155 and from 4-benzyloxyphenacyl bromide prepared from 4-hydroxyacetophenone by benzylation and bromination with bromine or copper bromide using known methods, 5-(4-benzyloxy-phenyl)-7-[3-(3-chloro-1-propoxy)phenyl]-4-aminopyrrolo[2,3-d]pyrimidine, m.p. 143°–146° C., is obtained in an analogous sequence.

1.0 g of 5-(4-benzyloxyphenyl)-7-[3-(3-chloro-1-propoxy)phenyl]-4-aminopyrrolo[2,3-d]-pyrimidine and 0.22 g of imidazolyl sodium are heated to 60° C. in 25 ml of DMF and the mixture is stirred for 6 h. The mixture is then cooled to RT and treated with water, extracted 3 times with ethyl acetate and concentrated. The residue is suspended in ethyl acetate and, after filtration and drying under HV, 5-(4-benzyloxyphenyl)-7-[3-(3-(1-imidazolyl)propoxy) -phenyl]-4-aminopyrrolo[2,3-d]pyrimidine having an m.p. of 144°–147° C. is obtained.

0.9 g of 5-(4-benzyloxyphenyl)-7-[3-(3-(1-imidazolyl) propoxy)phenyl]-4-aminopyrrolo[2,3-d]-pyrimidine are hydrogenated in a hydrogen atmosphere at normal pressure and about 40° C. for 20 h in 40 ml of THF in the presence of 0.15 g of 10% palladium/carbon. After filtration through Celite and chromatography of the residue on silica gel (methylene chloride/methanol 9:1) 5-(4-hydroxyphenyl)-7-[3-(3-(1-imidazolyl)propoxy)phenyl]-4-amino-pyrrolo[2,3-d]pyrimidine (Rf=0.2 silica gel, methylene chloride/methanol 9:1) is obtained.

EXAMPLE 165

5-(4-Hydroxy-3-methylphenyl)-7-[3-(2-(1-imidazolyl) ethoxy)phenyl]-4-amino-pyrrolo[2,3-d]pyrimidine Starting from 3-(2-chloro-1-ethoxy)aniline prepared from 3-nitrophenol and chlorobromo-ethane with subsequent catalytic hydrogenation in analogy to Example 155 and from the 4-benzyloxy-3-methylphenacyl bromide prepared from 4-hydroxy-3-methylacetophenone by benzylation and bromination with bromine or copper bromide using known methods, 5-(4-benzyloxy-3-methylphenyl)-7-[3-(2-chloro-1-ethoxy)phenyl]-4-aminopyrrolo[2,3-d]-pyrimidine, m.p. 133°–135° C., is obtained in an analogous sequence.

0.7 g of 5-(4-benzyloxy-3-methylphenyl)-7-[3-(2-chloro-1-ethoxy)phenyl]-4-aminopyrrolo-[2,3-d]pyrimidine and 0.2 g of imidazolyl sodium are heated to 80° C. in 30 ml of DMF and the mixture is stirred for 5 h. It is then cooled to RT and concentrated. After chromatography on silica gel, 5-(4-benzyloxy-3-methylphenyl)-7-[3-(2-(1-imidazolyl) ethoxy)phenyl]-4-amino-pyrrolo[2,3-d]pyrimidine having an m.p. of 158°–160° C. is obtained.

0.4 g of 5-(4-benzyloxy-3-methylphenyl)-7-[3-(2-(1-imidazolyl)ethoxy)phenyl]-4-amino-pyrrolo[2,3-d] pyrimidine are hydrogenated in a hydrogen atmosphere at normal pressure and about 40° C. for 10 h in 20 ml of THF and 10 ml of ethanol in the presence of 0.2 g of 5% palladium/carbon. After filtration through Celite and crystallization of the residue from methylene chloride, 5-(4-hydroxy-3-methylphenyl)-7-[3-(2-(1-imidazolyl)ethoxy) phenyl]-4-aminopyrrolo[2,3-d]pyrimidine having an m.p. of 202°–204° C. is obtained.

EXAMPLE 166

5-(4-Hydroxy-3-methoxyphenyl)-7-[3-(2-(1-imidazolyl) ethoxy)phenyl]-4-amino-pyrrolo[2,3-d]pyrimidine Starting from the 3-(2-chloro-1-ethoxy)aniline prepared from 3-nitrophenol and chlorobromoethane with subsequent catalytic hydrogenation in analogy to Example 155 and from the 4-benzyloxy-3-methylphenacyl bromide prepared from 4-hydroxy-3-methoxy-acetophenone by benzylation and bromination with bromine or copper bromide using known methods, 5-(4-benzyloxy-3-methoxyphenyl)-7-[3-(2-chloro-1-ethoxy)phenyl]-4-aminopyrrolo-[2,3-d] pyrimidine, m.p. 168°–169° C., is obtained in an analogous sequence.

0.8 g of 5-(4-benzyloxy-3-methoxyphenyl)-7-[3-(2-chloro-1-ethoxy)phenyl]-4-aminopyrrolo-[2,3-d]pyrimidine and 0.2 g of imidazolyl sodium are heated to 80° C. in 30 ml of DMF and the mixture is stirred for 5 h. It is then cooled to RT and concentrated. After chromatography on silica gel, 5-(4-benzyloxy-3-methoxyphenyl)-7-[3-(2-(1-imidazolyl) ethoxy)phenyl]-4-aminopyrrolo[2,3-d]pyrimidine having an m.p. of 122°–124° C. is obtained.

0.6 g of 5-(4-benzyloxy-3-methoxyphenyl)-7-[3-(2-(1-imidazolyl)ethoxy)phenyl]-4-amino-pyrrolo[2,3-d] pyrimidine is hydrogenated in a hydrogen atmosphere at normal pressure and about 50° C. for 6 h in 20 ml of THF and 10 ml of ethanol in the presence of 0.2 g of 5% palladium/carbon. After filtration through Celite and crystallization of the residue from methylene chloride, 5-(4-hydroxy-3-methoxyphenyl)-7-[3-(2-(1-imidazolyl)ethoxy) phenyl]-4-aminopyrrolo[2,3-d]pyrimidine having an m.p. of 190° C. is obtained.

EXAMPLE 167

5-(3-Hydroxy-4-methoxyphenyl)-7-[3-(2-(1-imidazolyl) ethoxy)phenyl]-4-amino-pyrrolo[2,3-d]pyrimidine Starting from the 3-(2-chloro-1-ethoxy)aniline prepared from 3-nitrophenol and chlorobromoethane with subsequent catalytic hydrogenation in analogy to Example 155 and from the 4-benzyloxy-3-methylphenacyl bromide prepared from 4-methoxy-3-hydroxy-acetophenone by benzylation and bromination with bromine or copper bromide using known methods, in an analogous sequence 5-(3-benzyloxy-4-methoxyphenyl)-7-[3-(2-chloro-1-ethoxy)phenyl]-4-aminopyrrolo[2,3-d]pyrimidine is obtained, m.p. 170° C.

1.1 g of 5-(3-benzyloxy-4-methoxyphenyl)-7-[3-(2-chloro-1-ethoxy)phenyl]-4-aminopyrrolo-[2,3-d]pyrimidine and 0.3 g of sodium imidazole are heated to 85° C. in 30 ml of DMF and the mixture is stirred for 8 h. It is then cooled to RT and concentrated. After chromatography on silica gel, 5-(3-benzyloxy-4-methoxyphenyl)-7-[3-(2-(1-imidazolyl) ethoxy)phenyl]-4-amino-pyrrolo[2,3-d]pyrimidine having an m.p. of 150° C. is obtained.

0.75 g of 5-(3-benzyloxy-4-methoxyphenyl)-7-[3-(2-(1-imidazolyl)ethoxy)phenyl]-4-amino-pyrrolo[2,3-d] pyrimidine is hydrogenated in a hydrogen atmosphere at normal pressure and about 50° C. for 12 h in 20 ml of THF and 10 ml of ethanol in the presence of 0.2 g of 5% palladium/carbon. After filtration through Celite and crystallization of the residue from methylene chloride, 5-(3-hydroxy-4-methoxyphenyl)-7-[3-(2-(1-imidazolyl)ethoxy) phenyl]-4-aminopyrrolo[2,3-d]pyrimidine having an m.p. of 205°–207° C. is obtained.

EXAMPLE 168

5-(4-Hydroxy-3,5-dimethylphenyl)-7-[3-(2-(1-imidazolyl) ethoxy)phenyl]-4-aminopyrrolo[2,3-d]pyrimidine Starting from the 3-(2-chloro-1-ethoxy)aniline prepared from 3-nitrophenol and chlorobromoethane with subsequent catalytic hydrogenation in analogy to Example 155 and from the 4-benzyloxy-3,5-dimethylphenacyl bromide prepared from 4-hydroxy-3,5-dimethyl-acetophenone by benzylation and bromination with bromine or copper bromide using known methods, in an analogous sequence 5-(4-benzyloxy-3,5-dimethylphenyl)-7-[3-(2-chloro-1-ethoxy)phenyl]-4-aminopyrrolo[2,3-d]pyrimidine is obtained, m.p. 188°–190° C.

0.45 g of 5-(4-benzyloxy-3,5-dimethylphenyl)-7-[3-(2-chloro-1-ethoxy)phenyl]-4-amino-pyrrolo[2,3-d]pyrimidine and 0.11 g of sodium imidazole are heated to 85° C. in 10 ml of DMF and the mixture is stirred for 8 h. It is then cooled to RT and concentrated. The residue is treated with water and extracted with methylene chloride, and the organic phases are dried and concentrated. After crystallization of the residue from methylene chloride/ether, 5-(4-hydroxy-3, 5-dimethylphenyl)-7-[3-(2-(1-imidazolyl)ethoxy)phenyl]-4-aminopyrrolo[2,3-d]-pyrimidine having an m.p. of about 100° C. is obtained.

0.35 g of 5-(4-benzyloxy-3,5-dimethylphenyl)-7-[3-(2-(1-imidazolyl)ethoxy)phenyl]-4-amino-pyrrolo[2,3-d] pyrimidine is hydrogenated in a hydrogen atmosphere at normal pressure and about 50° C. for 2 h in 15 ml of THF and 10 ml of ethanol in the presence of 0.2 g of 5% palladium/carbon. After filtration through Celite and chromatography on silica gel using methylene chloride/methanol 10:1, after crystallization from methylene chloride, 5-(4-hydroxy-3,5-dimethylphenyl)-7-[3-(2-(1-imidazolyl) ethoxy)phenyl]-4-aminopyrrolo[2,3-d]-pyrimidine having an m.p. of 150°–152° C. is obtained.

EXAMPLE 169

5-(3-Methoxyphenyl)-7-[3-(2-(1-imidazolyl)ethoxy) phenyl]-4-aminopyrrolo-[2,3-d]pyrimidine Starting from the 3-(2-chloro-1-ethoxy)aniline prepared from 3-nitrophenol and chlorobromoethane with subsequent catalytic hydrogenation according to Example 155 and from 3-methoxyphenacyl bromide, in an analogous sequence 5-(3-methoxyphenyl)-7-[3-(2-chloro-1-ethoxy)phenyl]-4-aminopyrrolo[2,3-d]pyrimidine is obtained, m.p.160° C.

0.8 g of 5-(3-methoxyphenyl)-7-[3-(2-chloro-1-ethoxy) phenyl]-4-aminopyrrolo[2,3-d]-pyrimidine and 0.24 g of sodium imidazole are heated to 80° C. in 20 ml of DMF and stirred for 5 h. The mixture is then cooled to RT and treated with water, extracted 3 times with methylene chloride and concentrated. After chromatography on silica gel using methylene chloride/methanol 15:2 and crystallization from ether/methylene chloride, 5-(3-methoxy-phenyl)- 7-[3-(2-(1-imidazolyl)ethoxy)phenyl]-4-aminopyrrolo[2,3-d] pyrimidine having an m.p. of 138°–140° C. is obtained.

EXAMPLE 170

5-(3-Chlorophenyl)-7-[3-(2-(1-imidazolyl)ethoxy)phenyl]-4-amino-pyrrolo-[2,3-d]pyrimidine Starting from the 3-(2-chloro-1-ethoxy)aniline prepared from 3-nitrophenol and chlorobromoethane with subsequent catalytic hydrogenation according to Example 155 and from 3-chlorophenacyl bromide, in an analogous sequence 5-(3-chlorophenyl)-7-[3-(2-chloro-1-ethoxy)phenyl]-4-aminopyrrolo[2,3-d]pyrimidine is obtained, m.p. 175°–177° C.

0.4 g of 5-(3-methoxyphenyl)-7-[3-(2-chloro-1-ethoxy) phenyl]-4-aminopyrrolo[2,3-d]-pyrimidine and 0.12 g of sodium imidazole are heated to 80° C. in 10 ml of DMF and stirred for 5.5 h. The mixture is then cooled to RT and treated with water, extracted 3 times with methylene chloride and concentrated. After chromatography on silica gel using methylene chloride/methanol 15:1 and crystallization from ether/methylene chloride, 5-(3-chloro-phenyl)-7-[3-(2-(1-imidazolyl)ethoxy)phenyl]-4-aminopyrrolo[2,3-d] pyrimidine having an m.p. of 125°–127° C. is obtained.

EXAMPLE 171

5-(4-Hydroxyphenyl)-7-[3-(2-methoxyethoxy)phenyl]-4-aminopyrrolo[2,3-d]-pyrimidine m.p. 103°–112° C. The compound is prepared analogously to Example 155. The starting material used is 3-(2-methoxyethoxy)aniline. This is prepared by reaction of 3-fluoronitrobenzene with the sodium salt of 2-methoxyethanol and subsequent reduction of the nitro group to the amino group.

The following compounds are also prepared analogously to the preceding examples:

EXAMPLE 172

5-(3-Hydroxyphenyl)-7-[4-(2-aminoethoxy)phenyl]-4-aminopyrrolo[2,3-d]-pyrimidine

EXAMPLE 173

5-(3-Hydroxyphenyl)-7-[3-(2-aminoethoxy)phenyl]-4-aminopyrrolo[2,3-d]-pyrimidine

EXAMPLE 174

5-(4-Methoxyphenyl)-7-[3-(2-(1-imidazolyl)ethoxy) phenyl]-4-aminopyrrolo-[2,3-d]pyrimidine

EXAMPLE 175

5-(3-Methoxyphenyl)-7-[3-(2-(2-hydroxyethylamino) ethoxy)phenyl]-4-amino-pyrrolo[2,3-d]pyrimidine

EXAMPLE 176

5-(3-Hydroxyphenyl)-7-[3-(2-N,N-dimethylaminoethoxy) phenyl]-4-amino-pyrrolo[2,3-d]pyrimidine

EXAMPLE 177

5-(3-Hydroxyphenyl)-7-[3-(2-(2-hydroxyethylamino) ethoxy)phenyl]-4-amino-pyrrolo[2,3-d]pyrimidine

EXAMPLE 178

5-(3-Methoxyphenyl)-7-[4-(2-(2-hydroxyethylamino) ethoxy)phenyl]-4-amino-pyrrolo[2,3-d]pyrimidine.

EXAMPLE A–B

Pharmaceutical Compositions

Example A

Tablets, each containing 50 mg of active ingredient:
Composition (10,000 tablets)

Active ingredient 500.0 g
Lactose 500.0 g
Potato starch 352.0 g
Gelatin 8.0 g
Talc 60.0 g
Magnesium stearate 10.0 g
Silica (highly disperse) 20.0 g
Ethanol q.s.

The active ingredient is mixed with the lactose and 292 g of the potato starch and the mixture is moistened with an ethanolic solution of the gelatin and granulated through a sieve. After drying, the remainder of the potato starch, the magnesium stearate, the talc and the silica are admixed and the mixture is compressed to give tablets of weight 145 mg each and 50 mg active ingredient content, which, if desired, can be provided with breaking notches for finer adjustment of the dose.

Example B

Film-coated tablets, each containing 100 mg of active ingredient:
Composition (1,000 film-coated tablets)

Active ingredient 100.0 g
Lactose 100.0 g
Maize starch 70.0 g
Talc 8.5 g
Calcium stearate 1.5 g
Hydroxypropylmethylcellulose 2.36 g
Shellac 0.64 g
Water q.s.
Dichloromethane q.s.

The active ingredient, the lactose and 40 g of the maize starch are mixed. The mixture is moistened with a paste prepared from 15 g of maize starch and water (with warming) and granulated. The granules are dried and the remainder of the maize starch, the talc and the calcium stearate are mixed with the granules. The mixture is compressed to give tablets (weight: 280 mg each) and these are coated with a solution of the hydroxypropylmethyl-cellulose and of the shellac in dichloromethane (final weight of the film-coated tablets: 283 mg each).

What is claimed is:

1. A compound of the formula I in which

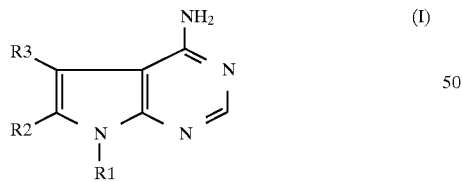

R₁ is phenyl which is unsubstituted or substituted by one or two substituents from the group consisting of lower alkyl, halo-lower alkyl, (hydroxy or lower alkanoyloxy)-lower alkyl, lower alkoxy-lower alkyl, (hydroxy, lower alkoxy or lower alkanoyloxy)-lower alkoxy-lower alkyl, (amino, lower alkylamino, di-lower alkylamino or lower alkanoylamino)-lower alkoxy-lower alkyl, (amino or lower alkanoylamino)-lower alkyl, lower alkylamino-lower alkyl, di-lower alkylamino-lower alkyl, (piperidinyl, piperazinyl, morpholinyl or pyrrolidinyl)-lower alkyl, (imidazoly, triazolyl, pyridyl, pyrimidinyl or pyrrolyl)-lower alkyl, (hydroxy, lower alkoxy or lower alkanoyloxy)-lower alkylamino-lower alkyl, (amino, lower alkylamino, di-lower alkylamino or lower alkanoylamino)-lower alkylamino-lower alkyl, (piperidinyl, piperazinyl, morpholinyl or pyrrolidinyl)-lower alkylamino-lower alkyl, (imidazolyl, triazolyl, pyridyl, pyrimidinyl or pyrrolyl)-lower alkylamino-lower alkyl, mercapto-lower alkyl, lower alkyl-(thio, sulfinyl or sulfonyl)-lower alkyl, (hydroxy, lower alkoxy or lower alkanoyloxy)-lower alkyl-(thio, sulfinyl or sulfonyl)-lower alkyl, (amino, lower alkylamino, di-lower alkylamino or lower alkanoylamino)-lower alkyl-(thio, sulfinyl or sulfonyl)-lower alkyl, carboxy-lower alkyl, lower alkoxycarbonyl-lower alkyl, aminocarbonyl-lower alkyl, N-lower alkylaminocarbonyl-lower alkyl, N,N-di-lower alkylaminocarbonyl-lower alkyl, hydroxyl, lower alkoxy, lower alkanoyloxy, $C_1$–$C_3$alkylenedioxy, phenyl-lower alkoxy, (hydroxy, lower alkoxy or lower alkanoyloxy)-lower alkoxy, (amino or lower alkanoylamino)-lower alkoxy, lower alkylamino-lower alkoxy, di-lower alkylamino-lower alkoxy, (piperidinyl, piperazinyl, morpholinyl or pyrrolidinyl)-lower alkoxy, (imidazolyl, triazolyl, pyridyl, pyrimidinyl or pyrrolyl)-lower alkoxy, (hydroxy, lower alkoxy or lower alkanoyloxy)-lower alkylamino-lower alkoxy, (amino, lower alkylamino, di-lower alkylamino or lower alkanoylamino)-lower alkylamino-lower alkoxy, (piperidinyl, piperazinyl, morpholinyl or pyrrolidinyl)-lower alkylamino-lower alkoxy, (imidazolyl, triazolyl, pyridyl, pyrimidinyl or pyrrolyl)-lower alkylamino-lower alkoxy, (hydroxy, lower alkoxy or lower alkanoyloxy)-lower alkoxy-lower alkoxy, (amino, lower alkylamino, di-lower alkylamino or lower alkanoylamino)-lower alkoxy-lower alkoxy, (hydroxy, lower alkoxy or lower alkanoyloxy)-lower alkyl-(thio, sulfinyl or sulfonyl)-lower alkoxy, (amino, lower alkylamino, di-lower alkylamino or lower alkanoylamino)-lower alkyl-(thio, sulfinyl or sulfonyl)-lower alkoxy, hydroxysulfonyl-lower alkoxy, carboxy-lower alkoxy, lower alkoxycarbonyl-lower alkoxy, aminocarbonyl-lower alkoxy, N-lower alkylaminocarbonyl-lower alkoxy, N,N-di-lower alkylaminocarbonyl-lower alkoxy, amino, lower alkylamino, di-lower alkylamino, lower alkanoylamino, piperidinyl, piperazinyl, morpholinyl, pyrrolidinyl, imidazolyl, triazolyl, pyridyl, pyrimidinyl, pyrrolyl, mercapto, lower alkyl-(thio, sulfinyl or sulfonyl), (hydroxy, lower alkoxy or lower alkanoyloxy)-lower alkyl-(thio, sulfinyl or sulfonyl), (amino, lower alkylamino, di-lower alkylamino or lower alkanoylamino)-lower alkyl-(thio, sulfinyl or sulfonyl), (hydroxy, lower alkoxy or lower alkanoyloxy)-lower alkoxy-lower alkyl-sulfinyl or sulfonyl), (amino, lower alkylamino, di-lower alkylamino or lower alkanoylamino)-lower alkoxy-lower alkyl-(thio, sulfinyl or sulfonyl), (hydroxy, lower alkoxy or lower alkanoyloxy)-lower alkylamino-lower alkyl-(thio, sulfinyl or sulfonyl), (amino, lower alkylamino, di-lower alkylamino or lower alkanoylamino)-lower alkylamino-lower alkyl-(thio, sulfinyl or sulfonyl), carboxy-lower alkylthio, lower alkoxycarbonyl-lower alkylthio, aminocarbonyl-lower alkylthio, N-lower alkylaminocarbonyl-lower alkylthio, N,N-di-lower alkylaminocarbonyl-lower alkylthio, halogen, carboxyl, lower alkoxycarbonyl, aminocarbonyl, N-lower alkylaminocarbonyl, N-[(hydroxy, lower alkoxy or lower alkanoyloxy)-lower alkyl]-aminocarbonyl, N-[(amino, lower alkylamino, di-lower alkylamino or lower alkanoylamino)-lower alkyl]-aminocarbonyl, N-[(piperidinyl, piperazinyl, morpholinyl or pyrrolidinyl)-lower alkyl]-aminocarbonyl, N-[(imidazolyl, triazolyl, pyridyl, pyrimidinyl or pyrrolyl)-lower alkyl]-aminocarbonyl, N-(hydroxysulfonyl-lower alkyl)-aminocarbonyl, N,N-di-lower alkylaminocarbonyl, cyano, amidino, formamidino and guanidino;

$R_2$ is hydrogen, lower alkyl or halogen; and $R_3$ is phenyl which is unsubstituted or substituted by one, two or three substituents from the group consisting of lower alkyl, hydroxy-lower alkyl, phenyl, hydroxyl, lower alkoxy, phenyl-lower alkoxy, $C_1$–$C_3$alkylenedioxy, cyano and halogen;

with the proviso that $R_3$ is other than phenyl, 4-methylphenyl, 4-methoxyphenyl and 4-chlorophenyl if $R_2$ is hydrogen and $R_1$ is phenyl, 4-methylphenyl, 4-methoxyphenyl, 4-chlorophenyl, 4-bromophenyl or 4-iodophenyl;

or a salt thereof.

2. A compound of the formula I according to claim 1, in which $R_1$ is phenyl which is unsubstituted or substituted by a substituent from the group consisting of lower alkyl, hydroxy-lower alkyl, lower alkanoyloxy-lower alkyl, halo-lower alkyl, amino-lower alkyl, lower alkylamino-lower alkyl, di-lower alkylamino-lower alkyl, (piperidinyl, piperazinyl, morpholinyl or pyrrolidinyl)-lower alkyl, (imidazolyl, triazolyl, pyridyl, pyrimidinyl or pyrrolyl)-lower alkyl, hydroxy-lower alkylamino-lower alkyl, amino-lower alkylamino-lower alkyl, (piperidinyl, piperazinyl, morpholinyl or pyrrolidinyl)-lower alkylamino-lower alkyl, (imidazolyl, triazolyl, pyridyl, pyrimidinyl or pyrrolyl)lower alkylamino-lower alkyl, mercapto-lower alkyl, lower alkyl-(thio, sulfinyl or sulfonyl)-lower alkyl, hydroxy-lower alkyl-(thio, sulfinyl or sulfonyl)-lower alkyl, amino-lower alkyl-(thio, sulfinyl or sulfonyl)-lower alkyl, hydroxyl, lower alkoxy, C1–C3alkylenedioxy, phenyl-lower alkoxy, hydroxy-lower alkoxy, lower alkoxylower alkoxy, lower alkanoyloxy-lower alkoxy, amino-lower alkoxy, lower alkylamino-lower alkoxy, di-lower alkylamino-lower alkoxy, (piperidinyl, piperazinyl, morpholinyl or pyrrolidinyl)-lower alkoxy, (imidazolyl, triazolyl, pyridyl, pyrimidinyl or pyrrolyl)-lower alkoxy, hydroxy-lower alkylamino-lower alkoxy, amino-lower alkylamino-lower alkoxy, (piperidinyl, piperazinyl, morpholinyl or pyrrolidinyl)-lower alkylamino-lower alkoxy, (imidazolyl, triazolyl, pyridyl, pyrimidinyl or pyrrolyl)-lower alkylamino-lower alkoxy, hydroxysulfonyl-lower alkoxy, amino, piperidinyl, piperazinyl, morpholinyl, pyrrolidinyl, imidazolyl, triazolyl, pyridyl, pyrimidinyl, pyrrolyl, mercapto, lower alkyl-(thio, sulfinyl or sulfonyl), hydroxy-lower alkyl-(thio, sulfinyl or sulfonyl), amino-lower alkyl-(thio, sulfinyl or sulfonyl), halogen, carboxyl, lower alkoxycarbonyl, aminocarbonyl, N-lower alkylaminocarbonyl, W(hydroxy-lower alkyl)-aminocarbonyl, N-(amino-lower alkyl)-aminocarbonyl, N-[(piperidinyl, piperazinyl, morpholinyl or pyrrolidinyl)-lower alkyl]-aminocarbonyl, N-[(imidazolyl, triazolyl, pyridyl, pyrimidinyl or pyrrolyl)-lower alkyl]-aminocarbonyl, N-(hydroxysulfonyl-lower alkyl)-aminocarbonyl, NA-di-lower alkylaminocarbonyl and cyano;

$R_2$ is hydrogen, lower alkyl or halogen; and $R_3$ is phenyl which is unsubstituted or substituted by one, two or three substituents from the group consisting of lower alkyl, hydroxy-lower alkyl, phenyl, hydroxyl, lower alkoxy, phenyllower alkoxy, $C_1$–$C_3$alkylenedioxy, cyano and halogen;

with the proviso that $R_3$ is other than phenyl, 4-methylphenyl, 4-methoxyphenyl and 4-chlorophenyl if $R_2$ is hydrogen and $R_1$ is phenyl, 4-methylphenyl, 4-methoxyphenyl, 4-chlorophenyl, 4-bromophenyl or 4-iodophenyl;

or a salt thereof;

or a pharmaceutically acceptable salt thereof.

3. A compound of the formula I according to claim 1, in which $R_1$ is phenyl which is unsubstituted or substituted by a substituent from the group consisting of lower alkyl, hydroxy-lower alkyl, halo-lower alkyl, amino-lower alkyl, lower alkylamino-lower alkyl, di-lower alkylamino-lower alkyl, (pyrimidinyl, piperazinyl or morpholinyl)-lower alkyl, (imidazolyl, triazolyl, pyridyl or pyrrolyl)-lower alkyl, hydroxy-lower alkylamino-lower alkyl, amino-lower alkylamino-lower alkyl, (pyrimidinyl, piperazinyl or morpholinyl)-lower alkylamino-lower alkyl, (imidazolyl, triazolyl, pyridyl or pyrrolyl)-lower alkylamino-lower alkyl, mercapto-lower alkyl, lower alkyl-(thio, sulfinyl or sulfonyl)-lower alkyl, hydroxy-lower alkyl(thio, sulfinyl or sulfonyl)-lower alkyl, amino-lower alkyl-(thio, sulfinyl or sulfonyl)-lower alkyl, hydroxyl, lower alkoxy, C1–C,3alkylenedioxy, phenyl-lower alkoxy, hydroxy-lower alkoxy, amino-lower alkoxy, lower alkylamino-lower alkoxy, di-lower alkylamino-lower alkoxy, (pyrimidinyl, piperazinyl or morpholinyl)-lower alkoxy, (imidazolyl, triazolyl, pyridyl or pyrrolyl)-lower alkoxy, hydroxy-lower alkylamino-lower alkoxy, amino-lower alkylamino-lower alkoxy, (pyrimidinyl, piperazinyl or morpholinyl)-lower alkylamino-lower alkoxy, (imidazolyl, triazolyl, pyridyl or pyrrolyl)-lower alkylamino-lower alkoxy, hydroxysulfonyl-lower alkoxy, amino, pyrimidinyl, piperazinyl, morpholinyl, imidazolyl, triazolyl, pyridyl, pyrrolyl, mercapto, lower alkyl-(thio, sulfinyl or sulfonyl), hydroxy-lower alkyl-(thio, sufinyl or sulfonyl), amino lower alkyl-(thio, sulfinyl or sulfonyl), halogen, carboxyl, lower alkoxycarbonyl, aminocarbonyl, N-lower alkylaminocarbonyl, W(hydroxy-lower alkyl)-aminocarbonyl, N-(amino-lower alkyl)-aminocarbonyl, N-((pyrimidinyl, piperazinyl or morpholinyl)-lower alkyl]-aminocarbonyl, N-((Imidazolyl, triazolyl, pyridyl or pyrrolyl)-lower alkyl]-aminocarbonyl, N-(hydroxysulfonyl-lower alkyl)-aminocarbonyl, N,N-di-lower alkylaminocarbonyl and cyano;

$R_2$ is hydrogen, lower alkyl or halogen; and $R_3$ is phenyl which is unsubstituted or substituted by a substituent from the group consisting of lower alkyl, phenyl, hydroxyl, lower alkoxy, phenyl-lower alkoxy, $C_1$–$C_3$alkylenedioxy, cyano and halogen;

with the proviso that $R_3$ is other than phenyl, 4-methylphenyl, 4-methoxyphenyl and 4-chlorophenyl if $R_2$ is hydrogen and $R_1$ is phenyl, 4-methylphenyl, 4-methoxyphenyl, 4-chlorophenyl, 4-bromophenyl or 4-iodophenyl;

or a salt thereof;

or a pharmaceutically acceptable salt thereof.

4. A method of therapeutically treating diseases selected from the group consisting of osteoporosis, tumour-induced hypercalcaemia, Paget's Disease, bone metastases, inflammation in joints and bones, degenerative processes in cartilaginous tissue, breast cancer, bowel cancer and thrombosis, comprising administering a therapeutically-effective amount of a compound of claim 1.

5. N-(2-Hydroxyethyl)-3-(5-phenyl-4-aminopyrrolo[2,3-d]pyrimidin-7-yl)benzamide according to claim 2 or a pharmaceutically acceptable salt thereof.

6. A method for preparing pharmaceutical compositions for the treatment of diseases selected from the group consisting of osteoporosis, tumour-induced hypercalcaemia, Paget's Disease, bone metastases, inflammation in joints and bones, degenerative processes in cartilaginous tissue, breast cancer, bowel cancer and thrombosis, comprising combining a therapeutically effective amount of a compound of claim 1 with a pharmaceutically acceptable carrier.

7. The method according to claim 4, wherein a compound of the formula I is used in which $R_1$ is phenyl which is unsubstituted or substituted by one or two substituents from the group consisting of lower alkyl, halo-lower alkyl, (hydroxy or lower alkanoyloxy)-lower alkyl, lower alkoxy-lower alkyl, (hydroxy, lower alkoxy or lower alkanoyloxy)-lower alkoxy-lower alkyl, (amino, lower alkylamino, di-lower alkylamino or lower alkanoylamino)-lower alkoxy-lower alkyl, (amino or lower alkanoylamino)-lower alkyl, lower alkylamino-lower alkyl, di-lower alkylamino-lower alkyl, (piperidinyl, piperazinyl, morpholinyl or pyrrolidinyl)-lower alkyl, (imidazolyl, triazolyl, pyridyl, pyrimidinyl or pyrrolyl)-lower alkyl, (hydroxy, lower alkoxy or lower alkanoyloxy)-lower alkylamino-lower alkyl, (amino, lower alkylamino, di-lower alkylamino or lower alkanoylamino)-lower alkylamino-lower alkyl, (piperidinyl, piperazinyl, morpholinyl or pyrrolidinyl)-lower alkylamino-lower alkyl, (imidazolyl, triazolyl, pyridyl, pyrimidinyl or pyrrolyl)-lower alkylamino-lower alkyl, mercapto-lower alkyl, lower alkyl-(thio, sulfinyl or sulfonyl)-lower alkyl, (hydroxy, lower alkoxy or lower alkanoyloxy)-lower alkyl-(thio, sulfinyl or sulfonyl)-lower alkyl, (amino, lower alkylamino, di-lower alkylamino or lower alkanoylamino)-lower alkyl-(thio, sulfinyl or sulfonyl)-lower alkyl, carboxy-lower alkyl, lower alkoxycarbonyl-lower alkyl, aminocarbonyl-lower alkyl, N-lower alkylaminocarbonyl-lower alkyl, N,N-di-lower alkylaminocarbonyl-lower alkyl, hydroxyl, lower alkoxy, lower alkanoyloxy, $C_1$–$C_3$alkylenedioxy, phenyl-lower alkoxy, (hydroxy, lower alkoxy or lower alkanoyloxy)-lower alkoxy, (amino or lower alkanoylamino)-lower alkoxy, lower alkylamino-lower alkoxy, di-lower alkylamino-lower alkoxy, (piperidinyl, piperazinyl, morpholinyl or pyrrolidinyl)-lower alkoxy, (imidazolyl, triazolyl, pyridyl, pyrimidinyl or pyrrolyl)-lower alkoxy; (hydroxy, lower alkoxy or lower alkanoyloxy)-lower alkylamino-lower alkoxy, (amino, lower alkylamino, di-lower alkylamino or lower alkanoylamino)-lower alkylamino-lower alkoxy, (piperidinyl, piperazinyl, morpholinyl or pyrrolidinyl)-lower alkylamino-lower alkoxy, (imidazolyl, triazolyl, pyridyl, pyrimidinyl or pyrrolyl)-lower alkylamino-lower alkoxy, (hydroxy, lower alkoxy or lower alkanoyloxy)-lower alkoxy-lower alkoxy, (amino, lower alkylamino, di-lower alkylamino or lower alkanoylamino)-lower alkoxy-lower alkoxy, (hydroxy, lower alkoxy or lower alkanoyloxy)-lower alkyl-(thio, sulfinyl or sulfonyl)-lower alkoxy, (amino, lower alkylamino, di-lower alkylamino or lower alkanoylamino)-lower alkyl-(thio, sulfinyl or sulfonyl)-lower alkoxy, hydroxysulfonyl-lower alkoxy, carboxy-lower alkoxy, lower alkoxycarbonyl-lower alkoxy, aminocarbonyl-lower alkoxy, N-lower alkylaminocarbonyl-lower alkoxy, N,N-di-lower alkylaminocarbonyl-lower alkoxy, amino, lower alkylamino, di-lower alkylamino, lower alkanoylamino, piperidinyl, piperazinyl, morpholinyl, pyrrolidinyl, imidazolyl, triazolyl, pyridyl, pyrimidinyl, pyrrolyl, mercapto, lower alkyl-(thio, sulfinyl or sulfonyl), (hydroxy, lower alkoxy or lower alkanoyloxy)-lower alkyl-(thio, sulfinyl or sulfonyl), (amino, lower alkylamino, di-lower alkylamino or lower alkanoylamino)-lower alkyl-(thio, sulfinyl or sulfonyl), (hydroxy, lower alkoxy or lower alkanoyloxy)-lower alkoxy-lower alkyl-(thio, sulfinyl or sulfonyl), (amino, lower alkylamino, di-lower alkylamino or lower alkanoylamino)-lower alkoxy-lower alkyl-(thio, sulfinyl or sulfonyl), (hydroxy, lower alkoxy or lower alkanoyloxy)-lower alkylamino-lower alkyl-(thio, sulfinyl or sulfonyl), (amino, lower alkylamino, di-lower alkylamino or lower alkanoylamino)-lower alkylamino-lower alkyl-(thio, sulfinyl or sulfonyl), carboxy-lower alkylthio, lower alkoxycarbonyl-lower alkylthio, aminocarbonyl-lower alkylthio, N-lower alkylaminocarbonyl-lower alkylthio, N,N-di-lower alkylaminocarbonyl-lower alkylthio, halogen, carboxyl, lower alkoxycarbonyl, aminocarbonyl, N-lower alkylaminocarbonyl, N-[(hydroxyl, lower alkoxy or lower alkanoyloxy)-lower alkyl]-aminocarbonyl, N-[(amino, lower alkylamino, di-lower alkylamino or lower alkanoylamino)-lower alkyl]-aminocarbonyl, N-[(piperidinyl, piperazinyl, morpholinyl or pyrrolidinyl)-lower alkyl]-aminocarbonyl, N-[(imidazolyl, triazolyl, pyridyl, pyrimidinyl or pyrrolyl)-lower alkyl]-aminocarbonyl; N-(hydroxysulfonyl-loweralkyl)-aminocarbonyl, N,N-di-lower alkylaminocarbonyl, cyano, amidino, formamidino and guanidino;

$R_2$ is hydrogen, lower alkyl or halogen; and $R_3$ is phenyl which is unsubstituted or substituted by one, two or three substituents from the group consisting of lower alkyl, hydroxy-lower alkyl, phenyl, hydroxyl, lower alkoxy, phenyl-lower alkoxy, $C_1$–$C_3$alkylenedioxy, cyano and halogen;

or a pharmaceutically acceptable salt thereof.

8. The method according to claim 4, characterized in that a compound of the formula I is used in which $R_1$ is phenyl, 4-methylphenyl, 4-methoxyphenyl, 4-chlorophenyl, 4-bromophenyl or 4-iodophenyl, $R_2$ is hydrogen and $R_3$ is phenyl, 4-methoxyphenyl or 4-chlorophenyl, or a pharmaceutically acceptable salt thereof.

9. A pharmaceutical composition containing a compound according to claim 1 and at least one pharmaceutically acceptable carrier.

* * * * *